(12) United States Patent
Singh et al.

(10) Patent No.: US 9,982,010 B2
(45) Date of Patent: May 29, 2018

(54) 7-DEHYDROCHOLESTEROL DERIVATIVES AND METHODS USING SAME

(71) Applicant: Women & Infants Hospital of Rhode Island, Providence, RI (US)

(72) Inventors: Rakesh K. Singh, Barrington, RI (US); Richard G. Moore, Cranston, RI (US)

(73) Assignee: Women & Infants Hospital of Rhode Island, Providence, RI (US)

( * ) Notice: Subject to any disclaimer, the term of this patent is extended or adjusted under 35 U.S.C. 154(b) by 0 days. days.

(21) Appl. No.: 15/302,898

(22) PCT Filed: Apr. 7, 2015

(86) PCT No.: PCT/US2015/024682
§ 371 (c)(1),
(2) Date: Oct. 7, 2016

(87) PCT Pub. No.: WO2015/157262
PCT Pub. Date: Oct. 15, 2015

(65) Prior Publication Data
US 2017/0029459 A1 Feb. 2, 2017

Related U.S. Application Data

(60) Provisional application No. 61/976,148, filed on Apr. 7, 2014.

(51) Int. Cl.
| | |
|---|---|
| *C07J 71/00* | (2006.01) |
| *A61K 31/401* | (2006.01) |
| *A61K 31/415* | (2006.01) |
| *A61K 31/565* | (2006.01) |
| *A61K 31/575* | (2006.01) |
| *A61K 31/58* | (2006.01) |
| *A61K 45/06* | (2006.01) |

(52) U.S. Cl.
CPC ......... *C07J 71/0042* (2013.01); *A61K 31/401* (2013.01); *A61K 31/415* (2013.01); *A61K 31/565* (2013.01); *A61K 31/575* (2013.01); *A61K 31/58* (2013.01); *A61K 45/06* (2013.01)

(58) Field of Classification Search
CPC ... A61K 31/401; A61K 31/415; A61K 31/565
See application file for complete search history.

(56) References Cited

U.S. PATENT DOCUMENTS

2004/0009958 A1   1/2004  Bishop et al.

OTHER PUBLICATIONS

Batta (Synthesis of [3a-3H]7-dehydrocholesterol via stable tritiated 4-phenyl-1,2,4-triazoline-3,5-dione derivative; Steriods 62(11): 700-702, 1997).*
Batta; Steroids; 62, 700-702, 1997.*
Berge (Journal of Pharmaceutical Sciences; vol. 66(1), 1977).*
International Search Report and the Written Opinion of the International Searching Authority, or the Declaration dated Jun. 29, 2015 for PCT/U52015/024682.
Balla et al. "Synthesis of [3a-3H]7-Dehydrocholesterol via Stable Tritiated 4-phenyl-1,2,4-triazoline-3,5-dione Derivative. Steriods" 62(11 ): 700-702, (1997).
K. Shimada, et al., "Retention behavior of Conjugated metabolites of Vitamin D and related Compounds in High-performance Liquid Chromatography", Journal of Chromatographic Sci., Oxford University Press., vol. 32, No. 3, pp. 107-111, (1994).
Extended European Search Report issued in European Application No. 15777532.1 dated Nov. 2, 2017.
JP 10-87690 A (Nisshin Flour Milling) Apr. 7, 1998 (Apr. 7, 1998) see machine translation.
Leigh et al., "Organic Reactions in Liquid-Crystalline Solvents. Regiochemical Control of Bimolecular Pericyclic Reactions by Cholesteric and Smectic Liquid-Crystalline Solvents." Journal of the American Chemical Society 114(13): 5005-5010, 1992. (2015).

* cited by examiner

*Primary Examiner* — Pancham Bakshi
(74) *Attorney, Agent, or Firm* — Saul Ewing Arnstein & Lehr LLP; Peter C. Lauro, Esq.

(57) ABSTRACT

The present invention provides, in certain aspects, novel 7-dehydrocholesterol (7DHC) derivatives that are useful in treating or preventing cancer, as well as in treating or preventing uncontrolled angiogenesis, in a subject. In certain embodiments of the present invention, the subject is a human. In other aspects, the present invention provides a method of preparing compounds of the invention, or a salt or solvate thereof.

15 Claims, 17 Drawing Sheets

|  | FP antagonist | Agonist |
|---|---|---|
| 7DHC | 9.814 ro 15.08 | NA |
| 7DHC-Adduct | NA | NA |
| Me7TC | 1.827 to 2.174 | NA |
| Cal-DT | NA | NA |

|  | VDR |
|---|---|
| 7DHC | >100 |
| 7DHC-Adduct | NA |
| Me7TC | 13.58 to 46.29 |
| Cal-DT | 20 |

7-DEHYDROCHOLESTEROL DERIVATIVES AND METHODS USING SAME

CROSS-REFERENCE TO RELATED APPLICATIONS

This application is the U.S. national phase, pursuant to 35 U.S.C. § 371, of PCT international application Ser. No. PCT/US2015/024682, filed Apr. 7, 2015, designating the United States and published in English on Oct. 15, 2015 as publication WO 2015/157262 A1, which claims priority under 35 U.S.C. § 119(e) to U.S. Provisional Application No. 61/976,148, filed Apr. 7, 2014. The entire contents of the aforementioned patent applications are hereby incorporated by reference in its entirety herein.

BACKGROUND OF THE INVENTION

Cancer, known medically as a malignant neoplasm, refers to a broad group of diseases involving unregulated cell growth. In cancer, cells divide and grow uncontrollably, forming malignant tumors and invading nearby parts of the body. The cancer may also spread to more distant parts of the body through the lymphatic system or bloodstream, through a mechanism generally known as metastasis. Not all tumors are cancerous, however. In contrast to cancerous tumors, benign tumors do not invade neighboring tissues and do not spread throughout the body.

Cancer is a highly heterogeneous disease, with over two hundred different known cancers that affect humans. The causes of cancer are diverse, complex, and only partially understood. Factors that increase the risk of cancer include tobacco use, dietary factors, certain infections, exposure to radiation, lack of physical activity, obesity, and environmental pollutants. These factors can directly damage genes or combine with existing genetic faults within cells to cause cancerous mutations. Approximately 5-10% of cancers can be traced directly to inherited genetic defects.

Cancer is the second leading cause of deaths in the U.S., and the number of deaths due to cancer continues to grow. Cancer treatment may include surgery, radiation and/or chemotherapy, based upon the type, location and dissemination of cancer. Surgery and localized radiation therapy may present lower toxicities to healthy cells and tissues, while chemotherapy is the best treatment option for disseminated cancer, leukemia, lymphoma, and metastasized cancers. Not all tumors respond to chemotherapeutic agents. Other tumors, although initially responsive to chemotherapeutic agents, may develop resistance, with cancer eventually recurring.

Various classes of chemotherapeutic agents have been described. These chemotherapeutic agents can be natural products, structurally modified natural products, or synthetic chemical or biological agents. The majority of chemotherapeutic drugs act by interfering with and/or preventing cell division, or interfering with DNA synthesis or function. Interestingly, novel tyrosine kinase inhibitors, such as imatinib mesylate (Gleevec or Glivec), target a specific molecular abnormality in specific types of cancer, and their use is thus limited to cancers that carry such abnormalities.

Angiogenesis is the physiological process through which new blood vessels form from pre-existing vessels. This is distinct from vasculogenesis, which is the de novo formation of endothelial cells from mesoderm cell precursors. Angiogenesis is a normal and vital process in growth and development, wound healing and the formation of granulation tissue. However, it is also a fundamental step in the transition of tumors from a benign state to a malignant one. Further, uncontrolled angiogenesis may damage various organs and tissues, such as eyes, skin, heart, blood vessels, lung, gastrointestinal tract and genitourinary tract. Thus, anti-angiogenesis agents (also known as angiogenesis inhibitors) may be used in the treatment of cancer and/or prevention of uncontrolled angiogenesis.

Cholesterol is a steroidal metabolite that is found in the cell membranes and transported in the blood plasma of all animals. Cholesterol is an essential structural component of mammalian cell membranes, where it is required to establish proper membrane permeability and fluidity. In addition, cholesterol is an important component for the manufacture of bile acids, steroid hormones, and fat-soluble vitamins including vitamins A, D, E and K.

Cholesterol accumulation has been reported in various solid tumors, including prostate cancer and oral cancer. In addition, cholesterol metabolism is dysregulated in many malignancies, including myeloid leukemia, lung cancer and breast cancer. Specifically, the activity of 3-hydroxy-3-methylglutaryl coenzyme A (HMG-CoA) reductase, the rate-limiting enzyme in cholesterol biosynthesis, is up-regulated in various tumors. Malignant cells often have elevated levels of mevalonate, which formation is catalyzed by HMG-CoA, and consistently mevalonate treatment was found to promote tumor growth in vivo and to stimulate the proliferation of breast cancer cells. Cholesterol metabolism is also dysregulated in many hematopoietic malignancies, including acute myeloid leukemia. High cellular cholesterol may in fact increase leukemia cell survival and impart relative resistance to therapy.

Cholesterol derivatives include 7-dehydrocholesterol (7DHC), a provitamin D present in animals. The presence of 7DHC in skin enables humans to manufacture vitamin D3 using ultraviolet rays in the sun light. Increased levels of 7DHC and decreased levels of cholesterol were found in patients with Smith-Lemli-Opitz syndrome (SLOS), an autosomal recessive malformation syndrome associated with intellectual disability and behavioral problems. Unfortunately, only a few examples of synthetic derivatives of cholesterol are known, and their effects on biosynthetic, metabolic and catabolic pathways of cholesterol remain unexplored.

There is a need in the art to identify novel compounds that can be used to treat or prevent cancer in a subject. There is also a need in the art to identify novel compounds that can be used to treat or prevent uncontrolled angiogenesis in a subject. The present invention addresses and meets these needs.

BRIEF SUMMARY OF THE INVENTION

As described below, the present invention provides novel 7-dehydrocholesterol (7DHC) derivatives that are useful in treating or preventing cancer, as well as in treating or preventing uncontrolled angiogenesis, in a subject. In certain embodiments of the present invention, the subject is a human.

In one aspect, the invention provides compounds, or a salt or solvate thereof.

In another aspect, the invention provides a method of preparing compounds of the invention, or a salt or solvate thereof.

In yet another aspect, the invention provides a pharmaceutical composition comprising at least one compound of the invention and a pharmaceutically acceptable carrier.

In yet another aspect, the invention provides a method of preventing or treating cancer in a subject in need thereof, the method comprising administering to the subject a therapeutically effective amount of at least one compound of the invention or a salt or solvate thereof.

In yet another aspect, the invention provides a method of preventing, reversing or inhibiting angiogenesis in a subject in need thereof, the method comprising administering to the subject an effective amount of a pharmaceutical composition comprising at least one compound of the invention or a salt or solvate thereof.

In yet another aspect, the invention provides a method of diagnosing a disease or disorder in a subject in need thereof, the method comprising administering to the subject an effective amount of a pharmaceutical composition comprising at least one compound of the invention or a salt or solvate thereof.

In yet another aspect, the invention provides a method of inhibiting the activity of the vitamin D receptor (also known as calcitriol receptor), the method comprising contacting the receptor with an effective amount of at least one compound of the invention or a salt or solvate thereof.

In yet another aspect, the invention provides a method of inhibiting the activity of the vitamin D receptor (also known as calcitriol receptor) in a subject in need thereof, the method comprising administering to the subject an effective amount of a pharmaceutical composition comprising at least one compound of the invention or a salt or solvate thereof.

In yet another aspect, the invention provides a prepackaged pharmaceutical composition comprising at least one compound of the invention, or a salt or solvate thereof, an applicator, and an instructional material for use thereof.

In certain embodiments, the compound is a compound of formula (I), or a salt or solvate thereof:

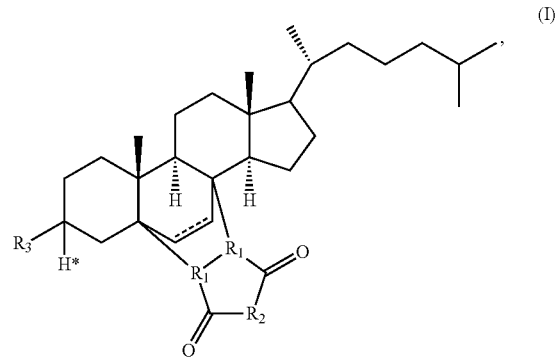

wherein in (I):
$R_1$ is $CR_5$ or N, wherein:
if $R_1$ is $CR_5$, then $R_3$ is selected from the group consisting of —$N(R_5)_2$, —NO, —$N(R_5)N(R_5)_2$, $R_6$, —$N(R_5)$—$OR_5$, —NH—$C(=O)R_5$, alkoxy, —$OSO_3H$, —$O(CR_5)_nR_6$, —$O(CR_5)_n$alkoxy, —$O(CR_5)_{n+1}OH$, —$OC(=O)(CR_5)_nR_6$, —$OC(=O)(CR_5)_nOR_5$, and —$OC(=O)C(R_5)=C(R_5)_2$; or $R_3$ is selected from the group consisting of =O and =S, and H* is omitted; and,
if $R_1$ is N, then $R_3$ is selected from the group consisting of $N(R_5)_2$, —NO, —$N(R_5)N(R_5)_2$, $R_6$, —$N(R_5)$—$OR_5$, —NH—$C(=O)R_5$, Cl, Br, I, alkoxy, mesyl, tosyl, —$O(CR_5)_nR_6$, —$O(CR_5)_{n+1}OR_5$, —$OC(=O)(CR_5)_nR_6$, —$OC(=O)(CR_5)_nOR_5$, and —$OC(=O)C(R_5)=C(R_5)_2$;

$R_2$ is selected from the group consisting of O, S, $C(R_4)_2$, and $N(R_4)$;
each occurrence of $R_4$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, substituted heteroarylalkyl, $OR_5$, and $N(R_5)_2$;
each occurrence of $R_5$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, and substituted heteroarylalkyl;
$R_6$ is selected from the group consisting of F, Cl, Br, I, mesyl, tosyl, —$OSi(R_5)_3$, —$C(=O)OR_5$, and —$C(=O)R_5$;
the dotted line is a single or double bond; and,
n is an integer ranging from 1 to 10.

In certain embodiments, the compound is a compound of formula (I):

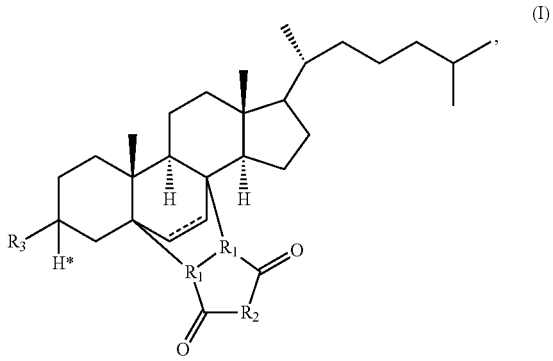

wherein in (I):
$R_1$ is $CR_5$ or N;
$R_3$ is selected from the group consisting of —$N(R_5)_2$, —NO, —$N(R_5)N(R_5)_2$, $R_6$, —$N(R_5)$—$OR_5$, —NH—$C(=O)R_5$, F, Cl, Br, I, hydroxy, alkoxy, mesyl, tosyl, —$OSO_3H$, —$O(CR_5)_nR_6$, —$O(CR_5)_n$alkoxy, —$O(CR_5)_{n+1}OH$, —$OC(=O)(CR_5)_nR_6$, —$OC(=O)(CR_5)_nOR_5$, and —$OC(=O)C(R_5)=C(R_5)_2$; or $R_3$ is selected from the group consisting of =O and =S, and H* is omitted;
$R_2$ is selected from the group consisting of O, S, $C(R_4)_2$, and $N(R_4)$;
each occurrence of $R_4$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, substituted heteroarylalkyl, $OR_5$, and $N(R_5)_2$;
each occurrence of $R_5$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, and substituted heteroarylalkyl;
$R_6$ is selected from the group consisting of F, Cl, Br, I, mesyl, tosyl, —$OSi(R_5)_3$, —$C(=O)OR_5$, and —$C(=O)R_5$;
the dotted line is a single or double bond; and,
n is an integer ranging from 1 to 10.

In certain embodiments, the compound of formula (I) is the compound of formula (Ia), or a salt or solvate thereof:

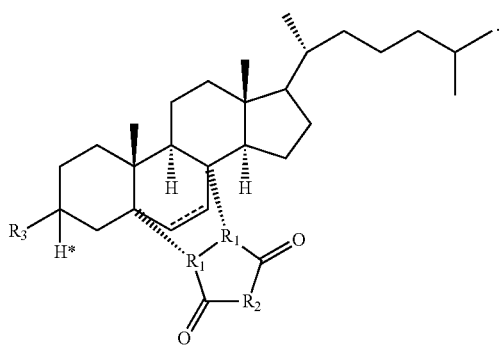

(Ia)

In certain embodiments, the compound of formula (I) is the compound of formula (Ib), or a salt or solvate thereof:

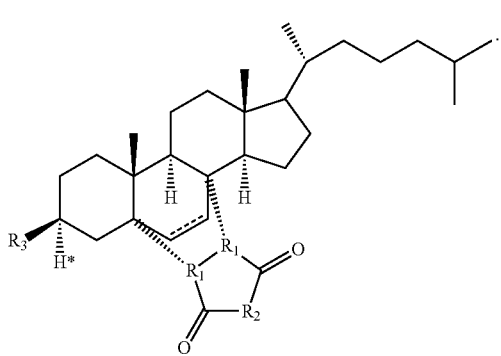

(Ib)

In certain embodiments, $R_1$ is N. In other embodiments, $R_2$ is $N(R_4)$.

In certain embodiments, the compound of formula (I) is the compound of formula (Ic), or a salt or solvate thereof:

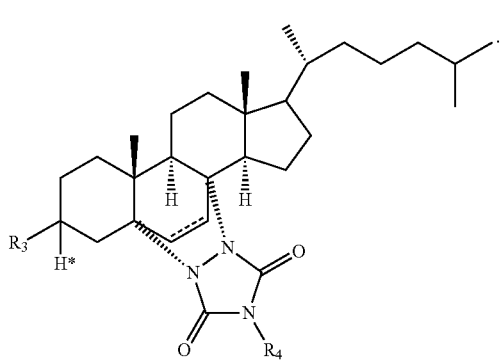

(Ic)

In certain embodiments, the compound of formula (I) is the compound of formula (Id), or a salt or solvate thereof:

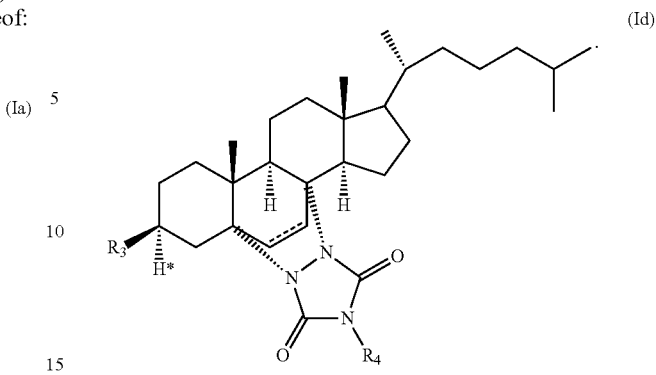

(Id)

In certain embodiments, $R_3$ is selected from the group consisting of —O(CR$_5$)$_n$R$_6$, —OC(=O)(CR$_5$)$_n$R$_6$, —OC(=O)(CR$_5$)$_n$OR$_5$, and —OC(=O)C(R$_5$)=C(R$_5$)$_2$.

In certain embodiments, the compound of formula (I) is selected from the group consisting of:

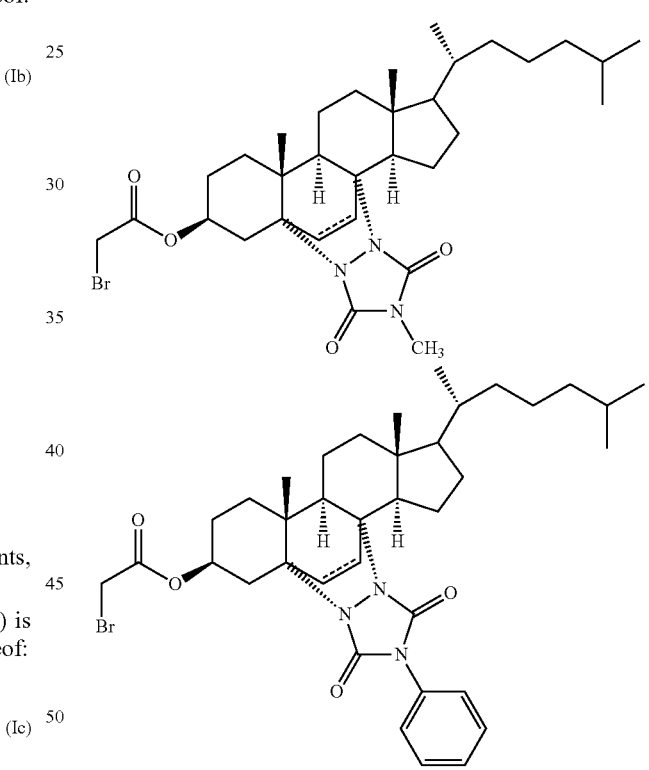

In certain embodiments, $R_1$ is $CR_5$. In other embodiments, $R_5$ is selected from the group consisting of H, alkyl, substituted alkyl, cycloalkyl, substituted cycloalkyl, arylalkyl, substituted arylalkyl, heteroarylalkyl, and substituted heteroarylalkyl. In yet other embodiments, $R_3$ is selected from the group consisting of $R_6$, —O(CR$_5$)$_n$R$_6$, OC(=O)(CR$_5$)$_n$R$_7$, and OC(=O)C(R$_5$)=C(R$_5$)$_2$; or $R^3$ is selected from the group consisting of =O and =S, and H* is omitted. In yet other embodiments, n is 1, 2, 3, 4 or 5. In yet other embodiments, the salt is an acid addition salt and is selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid, and any combinations thereof. In yet other embodiments, the salt is a base addition salt and is selected from the group consisting of calcium, magnesium, potassium, sodium, ammonium, zinc, a basic amine salt, and any combinations thereof, wherein the basic amine is selected from the group consisting of triethylamine, diisopropylethylamine, trimethylamine, N,N'-dibenzylethylene-diamine, chloroprocaine, choline, diethanolamine, ethylenediamine, meglumine, procaine and any combinations thereof.

In certain embodiments, the compound is administered to the subject as a pharmaceutical composition comprising at least one compound of the invention and a pharmaceutically acceptable carrier.

In certain embodiments, the composition further comprises at least one additional chemotherapeutic agent selected from the group consisting of alkylating agents; nitrosoureas; antimetabolites; antitumor antibiotics; plant alkyloids; taxanes; hormonal agents; anti-angiogenesis agents, and miscellaneous agents. In other embodiments, the composition further comprises at least one additional anti-angiogenesis agent selected from the group consisting of 2-methoxyestradiol AG3340, angiostatin, antithrombin-III, anti-VEGF antibody, VEGF antagonist, batimastat, bevacizumab, BMS-275291, CA1, canstatin, combretastatin, combretastatin-A4 phosphate, CC-5013, captopril, celecoxib, dalteparin, EMD121974, endostatin, erlotinib, gefitinib, genistein, halofuginone, ID1, ID3, IM862, omatinib mesylate, inducible protein-10, interferon-alpha, interleukin-12, lavendustin-a, LY317615, AE-941, merimastat, mapsin, medroxpregesteron acetate, Meth-1, Meth-2, Neovastat, osteopontin cleaved product, PEX, pigment epithelium growth factor, platelet growth factor 4, prolactin fragment, proliferin-related protein (PRP), PTK787/ZK222584, recombinant human platelet factor-4, restin, squalamine, SU5416, SU6668, suramin, taxol, tecogalan, thalidomide, thrombospondin, TNP-470, troponin I, vasostatin, VEGF1, VEGF-TRAP and ZD6474. In yet other embodiments, the compound and the agent are co-formulated in the composition.

In certain embodiments, the cancer comprises one selected from the group consisting of breast cancer, prostate cancer, ovarian cancer, cervical cancer, skin cancer, pancreatic cancer, colorectal cancer, renal cancer, liver cancer, brain cancer, lymphoma, leukemia, lung cancer, endometrial cancer, neuroblastoma, and any combinations thereof. In other embodiments, the cancer comprises one selected from the group consisting of prostate cancer, breast cancer, ovarian cancer, endometrial cancer, medulloblastoma, neuroblastoma, melanoma, and any combinations thereof.

In certain embodiments, the subject is further administered at least one additional chemotherapeutic agent. In other embodiments, the subject is further administered at least one additional anti-angiogenesis agent. In yet other embodiments, the compound and the agent are separately administered to the subject. In yet other embodiments, the compound and the agent are co-administered to the subject. In yet other embodiments, the subject is a mammal. In yet other embodiments, the mammal is a human. In yet other embodiments, the composition is administered to the subject by at least one route selected from the group consisting of intra-venous, oral, inhalational, rectal, vaginal, transdermal, intranasal, buccal, sublingual, parenteral, intrathecal, intragastrical, ophthalmic, pulmonary and topical routes.

In certain embodiments, the method further comprises procuring the compound of the invention for the subject.

In certain embodiments, the method of preparing a compound of the invention comprises reacting a compound of formula (II) with a compound of formula (III):

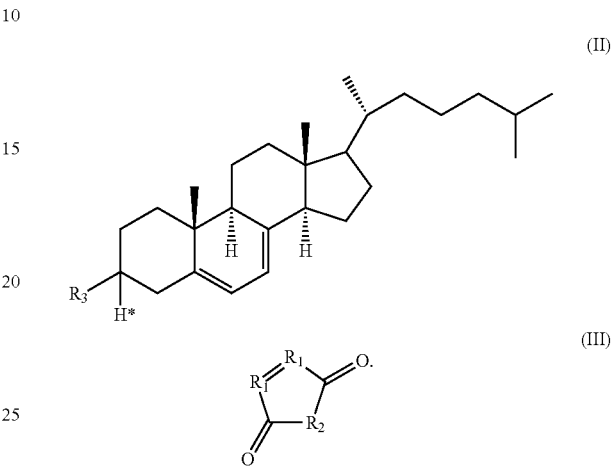

In other embodiments, the compounds of formula (II) and (III) are reacted in the dark or under reduced light conditions.

In certain embodiments, the instructional material comprises instructions for preventing, treating or inhibiting cancer or angiogenesis in a subject. In other embodiments, the prepackaged pharmaceutical composition further comprises at least one additional chemotherapeutic agent or an antiangiogenesis agent.

Other aspects, embodiments, advantages, and features of the present invention will become apparent from the following specification.

BRIEF DESCRIPTION OF THE DRAWINGS

The following detailed description of various embodiments of the invention will be better understood when read in conjunction with the appended drawings. For the purpose of illustrating the invention, there are shown in the drawings certain specific embodiments. It should be understood, however, that the invention is not limited to the precise arrangements and instrumentalities of the embodiments shown in the drawings.

FIG. 10A is a graph that illustrates antagonistic studies with VDR. FIG. 10B is a graph that illustrates agonistic studies with VDR. FIG. 10C is a table summarizing selected results of the present invention. FIG. 10D is a graph that illustrates results for the VDR transactivation assay (as % effect vs. log [Conc]). FIGS. 10E-10F are graphs that illustrate the determination of, respectively, antagonistic and agonistic properties of MeTC7 using a PPARγ-coactivator binding assay.

FIGS. 11A-11C illustrate viability of selected cell lines before and after MeTC7 treatment. FIGS. 11D-11E are a set of images illustrating effects of treatment of cell lines with compounds of the invention. FIG. 11F is a graph illustrating tumor size as a function of time (days). FIG. 11G is a graph illustrating survival proportion as a function of time (days). FIG. 11H is a graph illustrating average weight as a function of time (days). FIG. 11I is a set of images illustrating effects of compounds of the invention on xenografts.

DETAILED DESCRIPTION OF THE INVENTION

Figure 1:
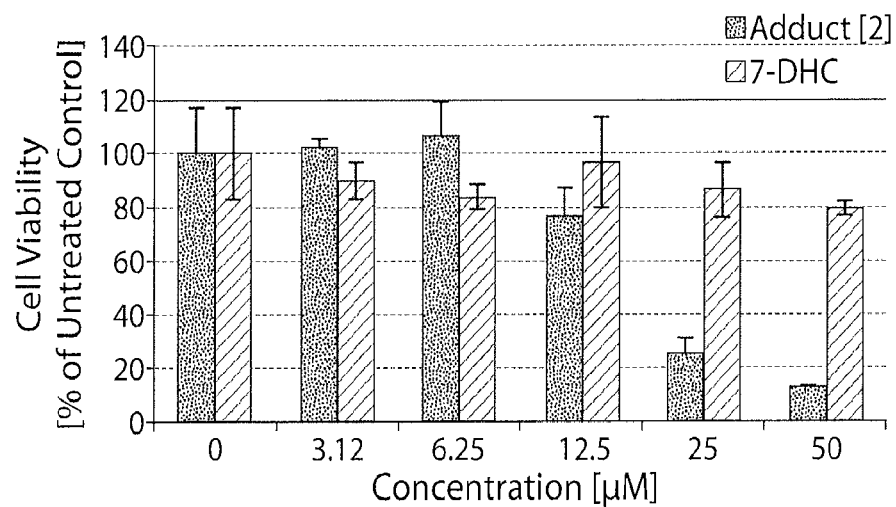
FIG. 1 is a bar graph illustrating the cell viability of SKOV-3 cells treated with 7-dehydrocholesterol and Compound (2).

The present invention relates to the unexpected identification of novel 7-dehydrocholesterol derivatives that are useful in treating or preventing cancer, as well as in treating or preventing uncontrolled angiogenesis in a subject. In certain embodiments of the present invention, the subject is a human.

As demonstrated herein, the compounds of the invention are potent cytotoxic agents against a wide variety of cancel cells. In a non-limiting example, selected compounds of the invention were shown to have $IC_{50}$ values ranging from 1 pM to 100 μM against ovarian and endometrial cancer cell lines. Further, in a preliminary cell viability assay, a compound of the invention demonstrated potent cytotoxic effects against a panel of cultured endometrial cancer cells (ECC-1, RL-95, AN3CA; $IC_{50}$<100 nM) and ovarian cancer cells (SKOV-3; $IC_{50}$<100 nM), prostate cancer cells (PC-3; $IC_{50}$<100 nM), neuroblastoma cells (SMSKCNR; $IC_{50}$<10 μM) and breast cancer cells (MCF-7; $IC_{50}$>20 μM) cells within 24 hours. Further, a compound of the invention reduced the cell viability of MCF-7 cancer cells ($IC_{50}$<20 μM) within 72 hours of treatment.

In contrast, a much higher concentration of the compounds of the invention was required to affect viability of normal trimester trophoblastic cells (TCL-1), indicating that the compounds of the invention display high therapeutic and safety.

Without wishing to be limited by any theory, in certain aspects, the compounds of the invention inhibit lipid synthesis in a cancer cell selectively. Normal cells generally do not perform their own de novo lipid synthesis, rather depending on dietary fat uptake. On the other hand, cancer cells often conduct de novo lipid synthesis to aid their rapid proliferation and energy needs. In certain embodiments, the compounds of the invention interfere with the de novo lipid synthesis in cancer cells, inhibiting tumor growth and reducing tumor burden, without concomitant off-target toxicity.

Without wishing to be limited by any theory, in certain aspects, the compounds of the invention act as antagonists of the Vitamin D receptor (also known as calcitriol receptor).

In certain embodiments of the invention, the compounds of the invention are used to reduce obesity and obesity-induced disorders, such as diabetes and cardiovascular diseases.

In certain embodiments of the invention, the compounds of the invention are used to treat cholesterol disorders.

In certain embodiments of the invention, the compounds of the invention are used to treat patients suffering from Smith-Lemli-Opitz syndrome (SLOS).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the certain specific methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more advantageously ±5%, even more advantageously ±1%, and still more advantageously ±0.1% from the specified value, as such variations are appropriate to perform the disclosed methods.

As used herein, the term "7DHC" refers to 7-dehydrocholesterol.

As used herein, the term "DMSO" refers to dimethylsulfoxide.

As used herein, the term "PBST" refers to phosphate buffered saline solution with Tween 20.

As used herein, the term "DMEM" refers to Dulbecco's modified Eagle's medium.

As used herein, the term "RPMI" refers to Roswell Park Memorial Institute medium.

As used herein, the term "MTS" refers to (3-(4,5-dimethylthiazol-2-yl)-5-(3-carboxymethoxyphenyl)-2-(4-sulfophenyl)-2H-tetrazolium) or a salt thereof.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

As used herein, the term "cancer" is defined as disease characterized by the rapid and uncontrolled growth of aberrant cells. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, endometrial cancer, neuroblastoma, medulloblastoma, melanoma, and the like.

Non-limiting examples of solid cancers are breast, ovarian, endometrial, cervical, neuroblastoma, medulloblastoma, lung cancer, colon cancer, CNS cancer, melanoma, renal, prostate, medulloblastoma, head and neck cancer, esophagus cancer, pancreatic cancer, skin cancer, thyroidal cancer, peripheral nerve sheath cancer, ependymoma, cranaiopharyngioma, astrocytoma (juvenile pilocytic astrocytoma, subependymal giant cell astrocytoma, pleimorphic xanthoastrocytoma, analplastic astrocytoma, or gliomatosis cerebri), meningioma, germinoma, glioma, mixed glioma, choroid plexus tumor, oligodendroglioma, peripheral neuroectodermal tumors, CNS lymphoma, pituitary adenoma, or shwannoma.

As used herein, the term "carcinoma" refers to any cancer of epithelial origin. Non-limiting examples of carcinomas include, but are not limited to, acinar carcinoma, acinous carcinoma, alveolar adenocarcinoma, carcinoma adenomatosum, adenocarcinoma, carcinoma of adrenal cortex, alveolar carcinoma, alveolar cell carcinoma, basal cell carcinoma, carcinoma basocellulare, basaloid carcinoma, basosquamous cell carcinoma, breast carcinoma, branchioalveolar carcinoma, bronchiolar carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliate adenoids, carcinoma exulcere, carcinoma fibrosum, gelatinform carcinoma, gelatinous carcinoma, giant cell carcinoma, gigantocellulare, glandular carcinoma, granulose cell carcinoma, hair matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lentivular carcinoma, carcinoma lenticulare, lipomatous carcinoma, lymphoepithelial carcinoma, carcinoma mastotoids, carcinoma medullare, medullary carcinoma, carcinoma melanodes, melanotonic carcinoma, mucinous carcinoma, carcinoma muciparum, carcinoma mucocullare, mucoepidermoid carcinoma, mucous carcinoma, carcinoma myxomatodes, masopharyngeal carcinoma, carcinoma nigrum, oat cell carcinoma, carcinoma ossificans, osteroid carcinoma, ovarian carcinoma, papillary carcinoma, periportal carcinoma, preinvasive carcinoma, prostate carcinoma, renal cell carcinoma of kidney, reserve cell carcinoma, carcinoma sarcomatodes, scheinderian carcinoma, scirrhous carcinoma, carcinoma scrota, signet-ring cell carcinoma, carcinoma simplex, small cell carcinoma, solandoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberrosum, tuberous carcinoma, verrucous carcinoma, or carcinoma vilosum.

As used herein, the term "sarcoma" refers to any mesenchymal neoplasm that arises in bone and soft tissues. Non-limiting examples of sarcomas include liposarcomas (including myxoid liposarcomas and pleiomorphic liposarcomas), leiomyosarcomas, rhabdomyosarcomas, neurofibrosarcomas, malignant peripheral nerve sheath tumors, Edwing's tumors (including Edwing's sarcoma of bone, extraskeletal or non-bone) and primitive neuroectodermal tumors (PNET), synovial sarcoma, hemangiendothelioma, fibrosarcoma, desmoids tumors, dermatofibrosarcoma protuberance (DFSP), malignant fibrous histiocytoma (MFH), hemangiopericytoma, malignant mesenchymoma, alveolar soft-part sarcoma, epitheloid sarcoma, clear cell sarcoma, desmoplastic small cell tumor, gastrointestinal stromal tumor (GIST) and osteosarcoma, and chondrosarcoma.

As used herein, the term "refractory cancer" refers to a cancer that is resistant to the ordinary standards of care prescribed. These cancers, although potentially initially responsive to treatment, recur and/or may be completely non-responsive to the treatment.

As used herein, the term "immunogenic cancer" refers to cancers selected from the group consisting of malignant melanoma and renal cell carcinoma, Mantel cell lymphoma, follicular lymphoma, diffuse large B-cell lymphoma, T-cell acute lymphoblastic leukemia, Burkitt Lymphoma, myeloma, immunocytoma, acute promyelocytic leukemia, chronic myeloid/acute lyphoblastic leukemia, acute leukemia, B-cell acute lymphoblastic leukemia, anaplastic large cell leukemia, myelodysplastic syndrome/acute myeloid leukemia, non-Hodgkin's lymphoma, chronic lymphocytic leukemia, acute myelogenous leukemia (AML), common (pre-B) acute lymphocytic leukemia, malignant melanoma, T-cell lymphoma, leukemia, B-cell lymphoma, epithelial malignancies, lymphoid malignancies, gynecologic carcinoma, biliary adenocarcinomas and ductal adenocarcinomas of the pancreas.

As used herein, the term "chemotherapeutic agent" refers to a compound or composition that may be used to treat or prevent cancer. Non-limiting examples of these agents are DNA damaging agents, such astopoisomerase inhibitors (for example, etoposide, camptothecin, topotecan, irrinotecan, teniposide, mitoxantrone), anti-microtubule agents (for example, vincristine, vinblastine), antimetabolite agents (for example, cytarabine, methotrexate, hydroxyurea, 5-fluorouracil, flouridine, 6-thioguanine, 6-mercaptompurine, fludaribine, pentostatin, cholorodeoxyadenosine), DNA alkylating agents (for example, cisplatin, mecholorethamine, cyclophosphamide, ifosphamide, melphalan, chlorumbucil, busulfan, thiotepa, carmustine, lomustine, carboplatin, dacarbazine, procarbazine) and DNA strand break inducing agents (for example, bleomycin, doxarubicine, daunorubicine, idarubicine, mitomycin C). Chemotherapeutic agents include but are not limited to avicin, aclarubicin, acodazole, acronine, adozelesin, adriamycin, aldesleukin, alitretnoin, allopurinl sodium, altretamine, ambomycin, amitantrone acetate, aminoglutethimide, amscrine, anastrazole, annoceous acetogenins, anthramycin, asimicin, asparaginase, asperlin, azacitidine, azetepa, azotomycin, batimstat, benzodepa, bexarotene, bicalutamide, bisantrene, bisanafide, bizelesin, bleomycin, brequinar, brompirimine, bullatacin, busulfan, cabergoline, cactinomycin, calusterone, caracemide, carbetimer, carbopltin, carmustine, carubicin, carzelesin, cedefingol, chlorumbucil, celecoxib, cirolemycin, cisplatin, cladiribine, crisnatol, cyclophosphamide, cytarabine, dacarbazine, DACA, dactinomycin, daunorubicine, daunomycin, decitabine, denileukine, dexormaplatin, dezaguanine, diaziqone, docetaxel, doxarubicin, droloxifene, dromostalone, duazomycin, edatrexate, eflornithin, elsamitrucin, estramustine, etanidazole, etoposide, etropine, fadrozole, fazarabine, feneretinide, floxuridine, fludarabine, flurouracil, fluorocitabine, 5-FdUMP, fosquidone, fosteuecine, FK-317, FK-973, FR-66979, FR-900482, gemcitabine, gemtuzumab, ozogamicin, Gold Au198, goserelin, guanacone, hydroxyurea, idarubicine, ilmofosine, interferon alpha and analogs, iprolatin, irinotecan, lanreotide, letrozole, leuprolide, liarozole, lometrexol, lomustine, losoxantrone, masoprocol, maytansine, maturedepa, mecholoroethamine, megesterol, melengesterol, melphalan, menogaril, metoprine, mycophenolic acid, mitindomide, mitocarcin, mitogillin, mitomalacin, mitomycin, mitomycin C, mitosper, mitotane, mitoxantrone, nocodazole, nogalamycin, oprelvekin, ormaplatin, profiromycin, oxisuran, paclitaxel, pamidronate, pegaspargase, peliomycin, pentamustin, peplomycin, perfosfamide, pipobroman, piposulfan, piroxantrone, plicamycin, plomestane, porfimer, prednimustin, procarbazine, puromycin, pyrazofurin, riboprine, rogletimide, rituximab, rolliniastatin, safingol, samarium, semustine, simtrazene, sparfosate, sparcomycin, sulphofenur, spirogermanium, spiromustin, spiroplatin, squamocin, squamotacin, streptozocin, streptonigrin, SrCl$_2$, talosmycin, taxane, taxoid, tecoglan, temoprofin, tegafur, teloxantrone, teniposide, terxirone, testolactone, thiamiprine, thiotepa, thymitaq, tomudex, tiazofurin, tirapamazine, Top-53, topetecan, toremixifine, trastuzumab, trestolone, tricribine, trimetrexate, tricribine, trimetrexate glucuronate, triptorelin, tubulozole, uracil mustard, valrubicine, uredepa, vapreotide, vinblastin, vincristine, vindesin, vinepidine, zinostatin, vinglycinate, vinleurosine, vinorelbine, vinrosidine, vinzolidine, vorozole, zeniplatin, zorubicine, 2-chlorodeoxyrubicine, 2'-deoxyformycin, CEP-751, raltitrexed, N-propargyl-5,8-didezafolic acid, 2-chloro-2'-arabinofluoro-2'-deoxyadenosine, 2-chloro-2'-deoxyadenosine, 9-aminocamptothecin anisomycin, trichostatin, hPRL-G129R, linomide, sulfur mustard, N-methyl-N-nitrosourea, fotemustine, streptozotocin, bisplatinum, temozolomide, mitozolomide, AZQ, ormaplatin, CI-973, DWA2114R, JM216, JM335, tomudex, azacitidine, cytrabincine, gemcitabine, 6-mercaptopurine, teniposide, hypoxanthine, doxorubicine, CPT-11, daunorubicine, darubicin, epirubicine, nitrogen mustard, losoxantrone, dicarbazine, amscrine, pyrazoloacridine, all trans retinol, 14-hydroxy-retro-retinol, all-trans retinoic acid, N-(4-hydroxyphenyl) rertinamide, 13-cisretinoic acid, 3-methyl TTNEB, 9-cisretenoic acid, fludarabine, and 2-Cda.

Other chemotherapeutic agent include: adecylpenol, 20-epi-1,25-dihydroxyvitamin-D3, 5-ethynyl uracil, abiraterone, aclarubicine, acylfulvene, adozelecin, aldesleukin, ALL-TK antagonists, altretamine, ambumastine, amidox, amifostine, amino levulinic acid, anagralide, anastrozole, andrographolide, antagonist D, antarelix, anti-dorsalizing morphogenetic protein-1, antiandrogen, antiestrogen, antineoplastone, antisense oligonucleotides, aphidicolin, apoptosis gene modulators, apotosis regulators, apurinic acid, ara-cdp-dl-PTBA, arginine aminase, asulacrine, atamestine, atrimustine, axinamastine 1 and axinamastine 2, axinamastine 3, azasetron, azatoxin, azatyrosine, baccatin III derivatives, balanol, BCR/ABL antagonist, benzochlorins, benzoylsaurosporine, beta lactam derivatives, beta-alethine, perillyl alcohol, phenozenomycin, phenyl acetate, phosphatase inhibitors, picibanil, pilocarbine and salts or analogs thereof, pirarubucin, piritrexim, placetin A, placetin B, plasminogen activator inhibitor, platinum complex, phenyl ethyl isothiocyanate and analogs thereof, platinum compounds, platinum triamine complex, podophylotoxin, porfimer sodium, porphyromycin, propyl bis acridones, prostaglnadins J2, protease inhibitors, protein A based immune modulators, PKC ihibitors, microalgal, protein tyrosine phosphatase inhibitors, purine neucleoside phosphorylase inhibitors, purpurins, pyrazoloacridines, pyridoxylated haemoglobin polyoxyethylene conjugate, raf antagonists, raltitrexed, ramosetron, ras farnesyl protein tranaferase inhibitors, ras inhibitors, ras-GAP inhibitors, ratellitptine demethylated, Rhenium Re186 etidronate, rhizoxine, ribozyme, RII retinide, rogletimide, rosagliatazone and analogs and derivatives thereof, rohitukine, romurtide, roquinimex, rubiginone B1, ruboxyl, safingol, saintopin, SarCNU, sarcophytol A, sargrmostim, sdi 1 mimetics, semustine, senescence derived inhibitor 1, sense oligonucleotide, signal transduction inhibitors, signal transduction modulators, single chain antigen binfing protein, sizofiran, sobuzoxane, sodium borocaptate, sodium phenyl acetate, solverol, somatomedin binding protein, sonermin, sparfosic acid, spicamycin D, spiromustin, splenopentine, spongistatin 1, squalamine, stem cell inhibitor, stem cell division inhibitor, stipiamide, stromelysin, sulfinosine, superactive vasoactive intestinal peptide antagonists, suradista, siramin, swainsonine, synthetic glycosaminoglycans, tallimustine, tamoxifen methiodide, tauromustine, tazarotene, tacogalan sodium, tegafur, tellurapyrilium, telomerase inhibitors, temoporfin, tmeozolomide, teniposide, tetrachlorodecaoxide, tetrazomine, thaliblastine, thalidomide, thiocoraline, thrombopoetin and mimetics thereof, thymalfasin, thymopoetin receptor agonist, thymotrinan, thyroid stimulating harmone, tin ethyl etiopurpin, tirapazamine, titanocene and salts thereof, topotecan, topsentin, toremifene, totipotent stem cell factors, translation inhibitors, tretinoin, triacetyluridine, tricribine, trimetrexate, triptorelin, tropisetron, turosteride, tyrosine kinase inhibitors, tyrphostins, UBC inhibitors, ubenimex, urogenital sinus derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozol, zanoterone, zeniplatin, zilascorb and zinostatin.

Other chemotherapeutic agents include antiproliferative agents (e.g., piritrexim isothiocyanate), antiprostatic hypertrophy agents (sitogluside), Benign prostatic hyperplasia therapy agents (e.g., tomsulosine, RBX2258), prostate growth inhibitory agents (pentomone) and radioactive agents: fibrinogen I125, fludeoxyglucose F18, flurodopa F18, insulin I125, iobenguane I123, iodipamide sodium I131, iodoantipyrine I131, iodocholesterol I131, iodopyracet I125, iofetamine HCL I123, iomethin I131, iomethin I131, iothalamate sodium I125, iothalamate I131, iotyrosine I131, liothyronine I125, merosproprol Hg197, methyl ioodobenzo guanine (MIBG-I131 or MIBGI123) selenomethionine Se75, technetium Tc99m furifosmin, technetium Tc99m gluceptate, Tc99m biscisate, Tc99m disofenin, TC99m gluceptate, Tc99m lidofenin, Tc99m mebrofenin, Tc99m medronate and sodium salts thereof, Tc99m mertiatide, Tc99m oxidronate, Tc99m pentetate and salts thereof, Tc99m sestambi, Tc99m siboroxime, Tc99m succimer, Tc99m sulfur colloid, Tc99m teboroxime, Tc99m tetrofosmin, Tc99m tiatide, thyroxine I125, thyroxine I131, tolpovidone I131, triolein I125, treoline I125, and treoline 131.

Another category of chemotherapeutic agents is anticancer supplementary potentiating agents, e.g., antidepressant drugs (imipramine, desipramine, amitryptyline, clomipramine, trimipramine, doxepin, nortryptyline, protryptyline, amoxapine, and maprotiline), or no-trycyclic anti-depressant drugs (sertaline, trazodone and citalopram), $Ca^{++}$ antagonists (vermapil, nifedipine, nitrendipine and caroverine), calmodulin inhibitors (prenylamine, trifluroperazine and clomipramine), amphotericin B, triparanol analogs (e.g., tomoxifene), antiarrythmic drugs (e.g., quinidine), antihypertensive drugs (e.g., resepine), thiol depleters (e.g., buthionine and sulofoximine) and multiple drug resistance reducing agents such as cremaphor EL.

In certain embodiments, chemotherapeutic agents include annoceous acetogenins, ascimicin, rolliniastatin, guanocone, squamocin, bullatacin, squamotacin, axanes, baccatin, and taxanes (Paclitaxel and docetaxel).

In certain embodiments, chemotherapeutic agents include anti-CD20 mAB, rituximab, rituxan, tositumoman, Bexxar, anti-HER2, trastuzumab, Herceptin, MDX20, antiCA125 mAB, antiHE4 mAB, oregovomab mAB, B43.13 mAB, Ovarex, Breva-REX, AR54, GivaRex, ProstaRex mAB, MDX447, gemtuzumab ozoggamycin, Mylotarg, CMA-676, anti-CD33 mAB, anti-tissue factor protein, Sunol, IOR-05, C5, anti-EGFR mAB, anti-IFR1R mAB, MDX-447, anti-17-1A mAB, edrecolomab mAB, Panorex, anti-CD20 mAB (Y-90 lebelled), ibritumomab tiuxetan (IDEC-Y2B8), zevalin, and anti-idiotypic mAB.

As used herein, the term "uncontrolled angiogenesis" refers to angiogenesis that is not part of the normal or healthy development of novel blood vessels in a subject. Uncontrolled angiogenesis may be associated with cancer, ocular disease (for example, macular degeneration, maculopathy, diabetic retinopathy or retinopathy of prematurity (retrolental fibroplasia)), skin disease (for example, infantile hemangioma, verruca vulgaris, psoriasis, neurofibromatosis, or epidermolysis bullosa), autoimmune disease (for example, rheumatoid arthritis), gynecologic disease (for example, endometrial polyp, endometriosis, dysfunctional uterine bleeding, ovarian hyperstimulation syndrome, polycystic ovarian syndrome (PCO), or preeclamsia), cardiovascular disease (for example, coronary artery disease, ischemic cardiomyopathy, myocardial Ischemia, arteriosclerosis, atherosclerosis, athelosclerotic plaque, neovascularization, arterial occlusive disease, ischemia, ischemic ulcers, ischemic or post myocardial ischemia revascularization, peripheral vascular disease or intermittent claudication), gastrointestinal disease (for example, Crohn's disease and ulcerative colitis), buerger disease, thromboangitis obliterans, arteosclerosis obliterans, ischemic ulcers, multiple sclerosis, idiopathic pulmonary fibrosis, HIV infection, plantar faciitis, Von-Hippel Landou disease, CNS hemangioblastoma, retinal hemangioblastoma, thyroiditis, benign prostate hyperplasia, glomerulonephritis, ectopic pregnancy, and ectopic bone formation or keloid. In certain embodiments, the cancer may be biliary tract cancer, bladder cancer, bone cancer, brain cancer, choriocarcinoma, breast cancer, cervical cancer, colon and rectum cancer, connective tissue cancer, cancer of digestive system, endometrial, esophageal, eye cancer, fibromael, cancer of head and neck, gastric cancer, intra-epithelial neoplasm, kidney cancer, larynx cancer, leukemia including acute myeloid leukemia, acute lymphoid leukemia, chronic lymphoid leukemia, liver cancer, lung cancer (for example, small cell and non-small cell), lymphoma including Hodgkins or non-Hodgkins), melanoma, oral cavity cancer (lip, tongue, mouth and pharynx), ovarian cancer, pancreatic cancer, prostate cancer, retinoblastoma, rhabdomyosarcoma, rectal cancer, renal cancer and cancers of the respiratory tract, sarcoma, skin cancer, stomach cancer, testicular cancer, thyroid cancer, uterine cancer, cancers of the urinary system, a sarcoma or carcinoma.

The terms "patient," "subject" or "individual" are used interchangeably herein, and refer to any animal, or cells thereof whether in vitro or in situ, amenable to the methods described herein. In a non-limiting embodiment, the patient, subject or individual is a human.

As used herein, the term "procure" or "procuring" as relating to a subject in need of being administered a therapeutically active compound refers to the act of synthesizing, packaging, prescribing, purchasing and/or providing the compound so that the subject may be administered the compound.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

The term "prevent," "preventing" or "prevention," as used herein, means avoiding or delaying the onset of symptoms associated with a disease or condition in a subject that has not developed such symptoms at the time the administering of an agent or compound commences.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or calthrates thereof.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier is "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

In one aspect, the terms "co-administered" and "co-administration" as relating to a subject refer to administering to the subject a compound of the invention or salt thereof along with a compound that may also treat the disorders or diseases contemplated within the invention. In one embodiment, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

By the term "specifically bind" or "specifically binds," as used herein, is meant that a first molecule preferentially binds to a second molecule (e.g., a particular receptor or enzyme), but does not necessarily bind only to that second molecule.

As used herein, the term "VDR" refers to Vitamin D nuclear receptor.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Certain specific examples include ($C_1$-$C_6$)alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Certain specific examples include ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —NH$_2$, —N(CH$_3$)$_2$, (1-methyl-imidazol-2-yl), pyridin-2-yl, pyridin-3-yl, pyridin-4-yl, —C(=O)OH, trifluoromethyl, —C≡N, —C(=O)O(C$_1$-C$_4$)alkyl, —C(=O)NH$_2$, —C(=O)NH(C$_1$-C$_4$)alkyl, —C(=O)N((C$_1$-C$_4$)alkyl)$_2$, —SO$_2$NH$_2$, —C(=NH)NH$_2$, and —NO$_2$, advantageously containing one or two substituents selected from halogen, —OH, alkoxy, —NH$_2$, trifluoromethyl, —N(CH$_3$)$_2$, and —C(=O)OH, more advantageously selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. In certain embodiments, alkoxy includes (C$_1$-C$_3$)alkoxy, such as, but not limited to, ethoxy and methoxy.

As used herein, the term "halo" or "halogen" alone or as part of another substituent means, unless otherwise stated, a fluorine, chlorine, bromine, or iodine atom, advantageously, fluorine, chlorine, or bromine, more advantageously, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. In certain embodiments, aryl includes phenyl and naphthyl, in particular, phenyl.

As used herein, the term "aryl-(C$_1$-C$_3$)alkyl" means a functional group wherein a one to three carbon alkylene chain is attached to an aryl group, e.g., —CH$_2$CH$_2$-phenyl or —CH$_2$— phenyl (benzyl). Examples included aryl-CH$_2$— and aryl-CH(CH$_3$)—. The term "substituted aryl-(C$_1$-C$_3$)alkyl" means an aryl-(C$_1$-C$_3$)alkyl functional group in which the aryl group is substituted. Specific examples include substituted aryl(CH$_2$)—. Similarly, the term "heteroaryl-(C$_1$-C$_3$)alkyl" means a functional group wherein a one to three carbon alkylene chain is attached to a heteroaryl group, e.g., —CH$_2$CH$_2$-pyridyl. One embodiment is heteroaryl-(CH$_2$)—. The term "substituted heteroaryl-(C$_1$-C$_3$)alkyl" means a heteroaryl-(C$_1$-C$_3$)alkyl functional group in which the heteroaryl group is substituted. Specific examples include substituted heteroaryl-(CH$_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, in particular, straight.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Compounds and Compositions

The invention includes a compound of formula (I), or a salt or solvate thereof:

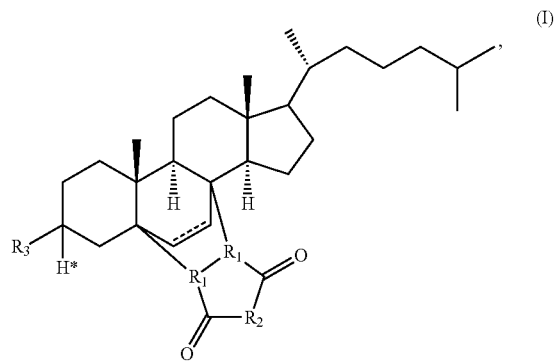

wherein in (I):

$R_1$ is $CR_5$ or N, wherein:

if $R_1$ is $CR_5$, then $R_3$ is selected from the group consisting of —$N(R_5)_2$, —NO, —$N(R_5)N(R_5)_2$, $R_6$, —$N(R_5)$—$OR_5$, —NH—C(=O)$R_5$, alkoxy, —$OSO_3H$, —$O(CR_5)_nR_6$, —$O(CR_5)_n$alkoxy, —$O(CR_5)_{n+1}OH$, —OC(=O)$(CR_5)_nR_6$, —OC(=O)$(CR_5)_nOR_5$, and —OC(=O)C($R_5$)=C($R_5$)$_2$;

or $R_3$ is selected from the group consisting of =O and =S, and H* is omitted; and, if $R_1$ is N, then $R_3$ is selected from the group consisting of $N(R_5)_2$, —NO, —$N(R_5)N(R_5)_2$, $R_6$, —$N(R_5)$—$OR_5$, —NH—C(=O)$R_5$, Cl, Br, I, alkoxy, mesyl, tosyl, —$O(CR_5)_nR_6$, —$O(CR_5)_{n+1}OR_5$, —OC(=O)$(CR_5)_nR_6$, —OC(=O)$(CR_5)_nOR_5$, and —OC(=O)C($R_5$)=C($R_5$)$_2$;

$R_2$ is selected from the group consisting of O, S, C($R_4$)$_2$, and N($R_4$);

each occurrence of $R_4$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, substituted heteroarylalkyl, $OR_5$, and $N(R_5)_2$;

each occurrence of $R_5$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, and substituted heteroarylalkyl;

$R_6$ is selected from the group consisting of F, Cl, Br, I, mesyl, tosyl, —OSi($R_5$)$_3$, —C(=O)$OR_5$, and —C(=O)$R_5$;

the dotted line is a single or double bond; and, n is an integer ranging from 1 to 10.

In certain embodiments, the dotted line is a single bond. In other embodiments, the dotted line is a double bond.

In certain embodiments, the compound of formula (I) is the compound of formula (Ia), or a salt or solvate thereof:

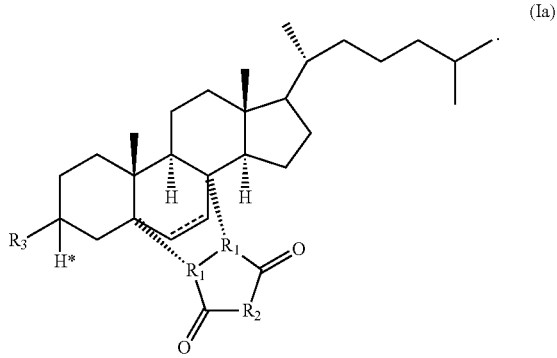
(Ia)

In certain embodiments, the compound of formula (I) is the compound of formula (Ib), or a salt or solvate thereof:

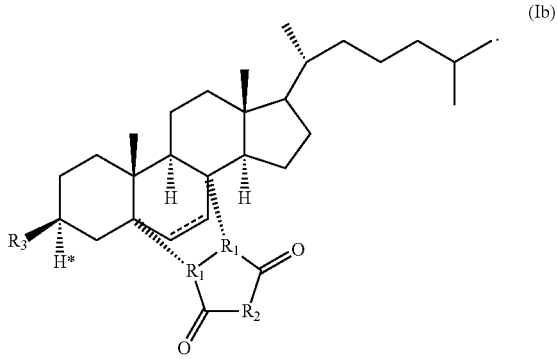
(Ib)

In certain embodiments, $R_1$ is N. In other embodiments, $R_2$ is $N(R_4)$.

In certain embodiments, the compound of formula (I) is the compound of formula (Ic), or a salt or solvate thereof:

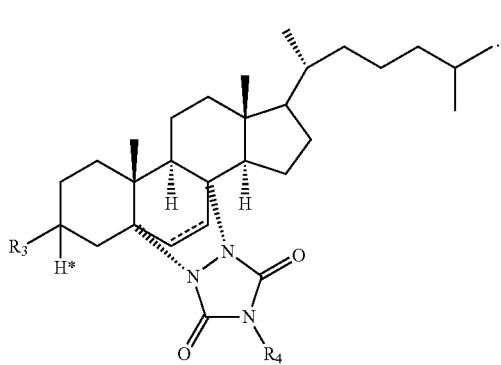
(Ic)

In certain embodiments, the compound of formula (I) is the compound of formula (Id), or a salt or solvate thereof:

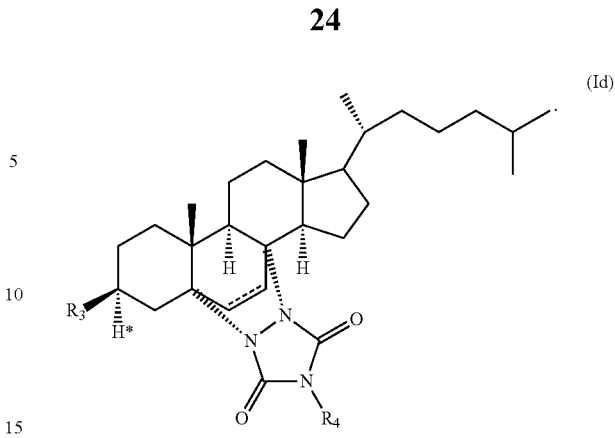
(Id)

In certain embodiments, $R_3$ is selected from the group consisting of —O(CR$_5$)$_n$R$_6$, —OC(=O)(CR$_5$)$_n$—R$_6$, —OC(=O)(CR$_5$)$_n$OR$_5$, and —OC(=O)C(R$_5$)=C(R$_5$)$_2$.

In certain embodiments, the compound of formula (I) is selected from the group consisting of:

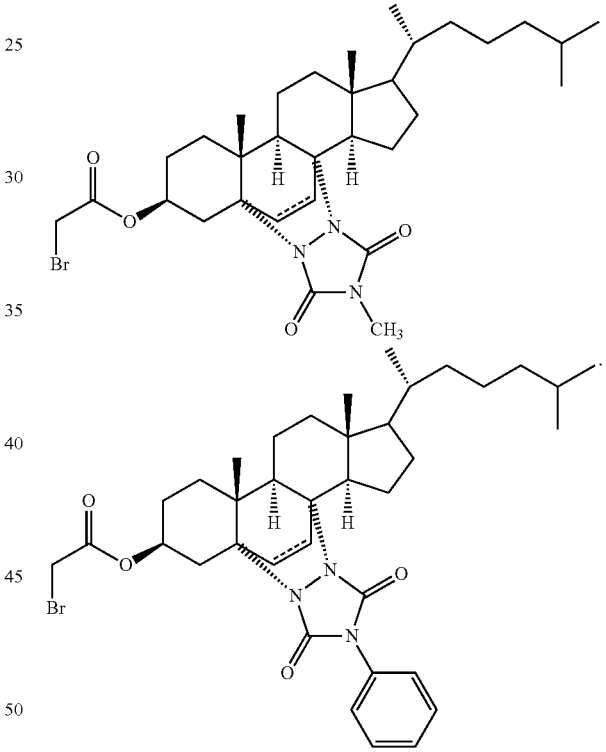

In certain embodiments, $R_1$ is $CR_5$. In other embodiments, $R_5$ is selected from the group consisting of H, alkyl, substituted alkyl, cycloalkyl, substituted cycloalkyl, arylalkyl, substituted arylalkyl, heteroarylalkyl, and substituted heteroarylalkyl. In yet other embodiments, $R_3$ is selected from the group consisting of $R_6$, —O(CR$_5$)$_n$R$_6$, OC(=O)(CR$_5$)$_n$R$_7$, and OC(=O)C(R$_5$)=C(R$_5$)$_2$; or $R^3$ is selected from the group consisting of =O and =S, and H* is omitted.

In certain embodiments, n is 1, 2, 3, 4 or 5.

In certain embodiments, the salt is an acid addition salt and is selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid, and any combinations thereof.

In certain embodiments, the salt is a base addition salt and is selected from the group consisting of calcium, magnesium, potassium, sodium, ammonium, zinc, a basic amine salt, and any combinations thereof, wherein the basic amine is selected from the group consisting of triethylamine, diisopropylethylamine, trimethylamine, N,N'-dibenzylethylene-diamine, chloroprocaine, choline, diethanolamine, ethylenediamine, meglumine, procaine and any combinations thereof.

The compounds of the invention may possess one or more stereocenters, and each stereocenter may exist independently in either the (R) or (S) configuration. In one embodiment, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention exist as tautomers. All tautomers are included within the scope of the compounds recited herein.

In one embodiment, compounds described herein are prepared as prodrugs (see for example Hacker, et al., Pharmacology: Principles and Practice. Academic Press, Jun. 19, 2009. pp. 216-217). A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. Accordingly, in one embodiment, a prodrug is created by methods well known in the art, by which the appropriate substituent to decrease or eliminate the susceptibility of the aromatic ring to metabolic reactions is added, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The invention further includes a pharmaceutical composition comprising the compound of the invention and a pharmaceutically acceptable carrier.

In certain embodiments, the pharmaceutical composition further comprises at least one additional chemotherapeutic agent selected from the group consisting of alkylating agents; nitrosoureas; antimetabolites; antitumor antibiotics; plant alkyloids; taxanes; hormonal agents; anti-angiogenesis agents, and miscellaneous agents.

In certain embodiments, the pharmaceutical composition further comprises at least one additional anti-angiogenesis agent. In other embodiments, the anti-angiogenesis agent is at least one selected from the group consisting of 2-methoxyestradiol AG3340, angiostatin, antithrombin-III, anti-VEGF antibody, VEGF antagonist, batimastat, bevacizumab, BMS-275291, CA1, canstatin, combretastatin, combretastatin-A4 phosphate, CC-5013, captopril, celecoxib, dalteparin, EMD121974, endostatin, erlotinib, gefitinib, genistein, halofuginone, ID1, ID3, IM862, omatinib mesylate, inducible protein-10, interferon-alpha, interleukin-12, lavendustin-a, LY317615, AE-941, merimastat, mapsin, medroxpregesteron acetate, Meth-1, Meth-2, Neovastat, osteopontin cleaved product, PEX, pigment epithelium growth factor, platelet growth factor 4, prolactin fragment, proliferin-related protein (PRP), PTK787/ZK222584, recombinant human platelet factor-4, restin, squalamine, SU5416, SU6668, suramin, taxol, tecogalan, thalidomide, thrombospondin, TNP-470, troponin I, vasostatin, VEGF1, VEGF-TRAP and ZD6474.

In certain embodiments, the compound of the invention and the additional agent are co-formulated in the composition.

Synthesis

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxy benzyl, while coexisting amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

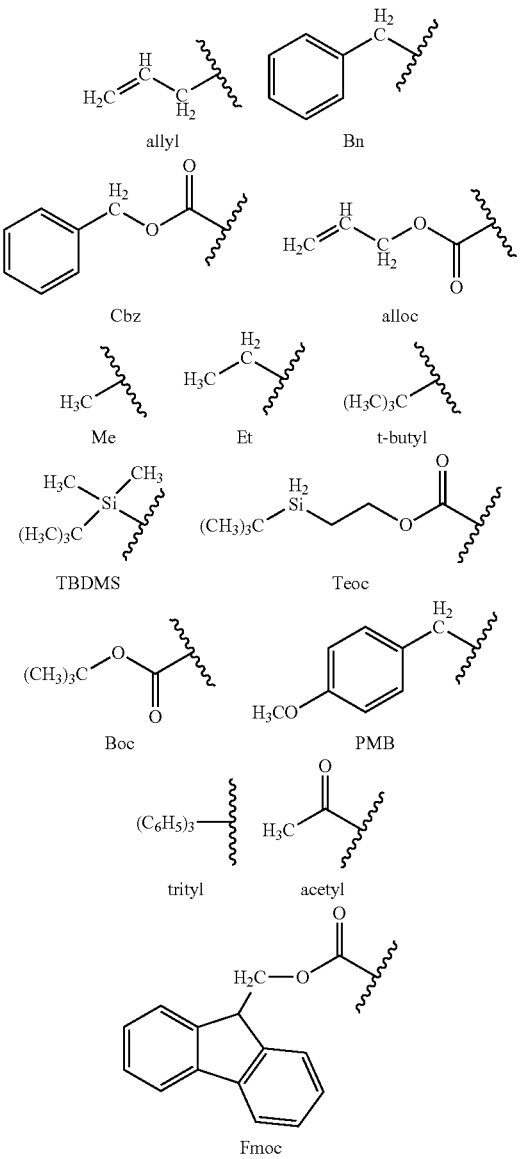

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

The compounds of the invention may be prepared according to the general methodology illustrated in the synthetic schemes described below. The reagents and conditions described herein may be modified to allow the preparation of the compounds of the invention, and such modifications are known to those skilled in the art. The scheme included herein are intended to illustrate but not limit the chemistry and methodologies that one skilled in the art may use to make compounds of the invention.

In certain embodiments, the compounds of the invention, or intermediates that are useful in preparing the compounds of the invention, may be generated using a Diels-Alder reaction between 7-hydrocholesterol, or a derivative thereof, such as compound (II), with a five-membered dienophile, such as compound (III):

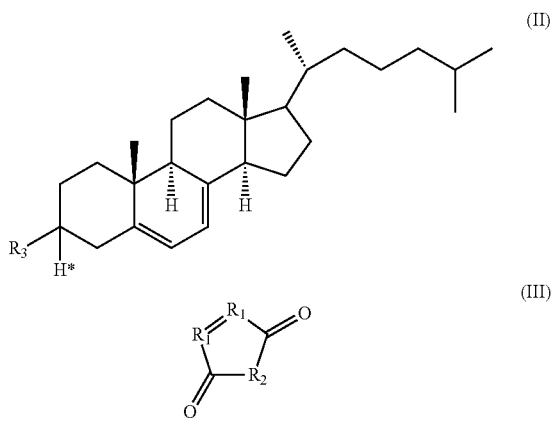

The product of the Diels-Alder reaction may be the compound of the invention, or may be further derivatized to yield a compound of the invention, as will be appreciated by those skilled in the art.

Salts

The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Methods

The invention includes a method of preventing or treating cancer in a subject in need thereof. The invention further includes a method of preventing, reversing or inhibiting angiogenesis in a subject in need thereof. The invention further includes a method of reducing obesity and obesity-induced disorders, such as diabetes and cardiovascular diseases, in a subject in need thereof. The invention further includes a method of treating cholesterol disorders in a subject in need thereof. The invention further includes a method of treating a patient suffering from Smith-Lemli-Opitz syndrome (SLOS). The invention further includes a method of diagnosing a disease or disorder in a subject in need thereof. The invention further includes a method of inhibiting activity of the vitamin D nuclear receptor. The invention further includes a method of inhibiting the activity of the vitamin D nuclear receptor (also known as calcitriol receptor) in a subject in need thereof.

In certain embodiments, the method comprises administering to the subject a therapeutically effective amount of at least one compound of formula (I) or a salt or solvate thereof:

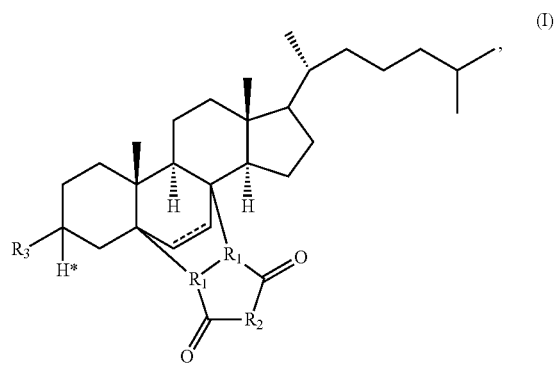

wherein in (I):

$R_1$ is $CR_5$ or N;

$R_3$ is selected from the group consisting of $-N(R_5)_2$, $-NO$, $-N(R_5)N(R_5)_2$, $R_6$, $-N(R_5)-OR_5$, $-NH-C(=O)R_5$, F, Cl, Br, I, hydroxy, alkoxy, mesyl, tosyl, $-OSO_3H$, $-O(CR_5)_nR_6$, $-O(CR_5)_n$alkoxy, $-O(CR_5)_{n+1}OH$, $-OC(=O)(CR_5)_nR_6$, $-OC(=O)(CR_5)_nOR_5$, and $-OC(=O)C(R_5)=C(R_5)_2$;

or $R_3$ is selected from the group consisting of $=O$ and $=S$, and H* is omitted;

$R_2$ is selected from the group consisting of O, S, $C(R_4)_2$, and $N(R_4)$;

each occurrence of $R_4$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, substituted heteroarylalkyl, $OR_5$, and $N(R_5)_2$;

each occurrence of $R_5$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, and substituted heteroarylalkyl;

$R_6$ is selected from the group consisting of F, Cl, Br, I, mesyl, tosyl, —OSi($R_5$)$_3$, —C(=O)O$R_5$, and —C(=O)$R_5$;

the dotted line is a single or double bond; and, n is an integer ranging from 1 to 10.

In certain embodiments, the method comprises contacting the vitamin D nuclear receptor with an effective amount of at least one compound of formula (I) or a salt or solvate thereof.

In certain embodiments, if $R_1$ is $CR_5$, then $R_3$ is selected from the group consisting of —N($R_5$)$_2$, —NO, —N($R_5$)N($R_5$)$_2$, $R_6$, —N($R_5$)—O$R_5$, —NH—C(=O)$R_5$, alkoxy, —OSO$_3$H, —O(C$R_5$)$_n$$R_6$, —O(C$R_5$)$_n$alkoxy, —O(C$R_5$)$_{n+1}$OH, —OC(=O)(C$R_5$)$_n$$R_6$, —OC(=O)(C$R_5$)$_n$O$R_5$, and —OC(=O)C($R_5$)=C($R_5$)$_2$; or $R_3$ is selected from the group consisting of =O and =S, and H* is omitted.

In certain embodiments, if $R_1$ is N, then $R_3$ is selected from the group consisting of N($R_5$)$_2$, —NO, —N($R_5$)N($R_5$)$_2$, $R_6$, —N($R_5$)—O$R_5$, —NH—C(=O)$R_5$, Cl, Br, I, alkoxy, mesyl, tosyl, —O(C$R_5$)$_n$$R_6$, —O(C$R_5$)$_{n+1}$O$R_5$, —OC(=O)(C$R_5$)$_n$$R_6$, —OC(=O)(C$R_5$)$_n$O$R_5$, and —OC(=O)C($R_5$)=C($R_5$)$_2$.

In certain embodiments, the compound of formula (I) is the compound of formula (Ia) or a salt or solvate thereof:

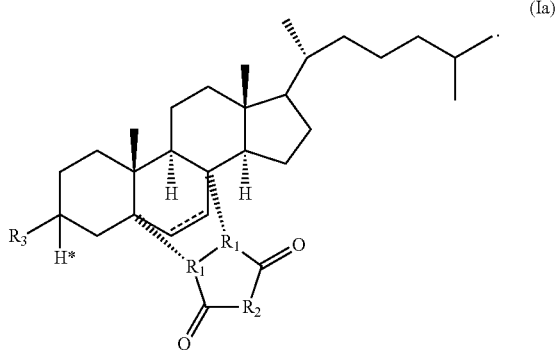

(Ia)

In certain embodiments, the compound of formula (I) is the compound of formula (Ib), or a salt or solvate thereof:

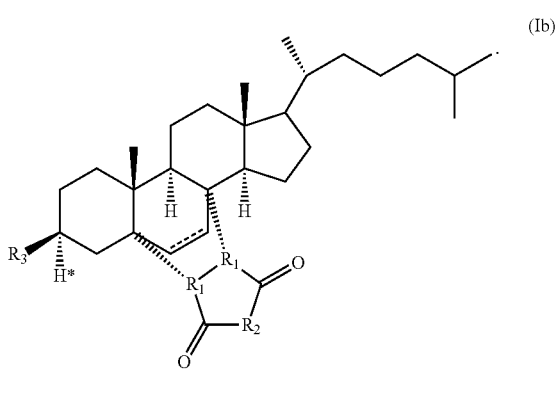

(Ib)

In certain embodiments, $R_1$ is N. In other embodiments, $R_2$ is N($R_4$).

In certain embodiments, the compound of formula (I) is the compound of formula (Ic), or a salt or solvate thereof:

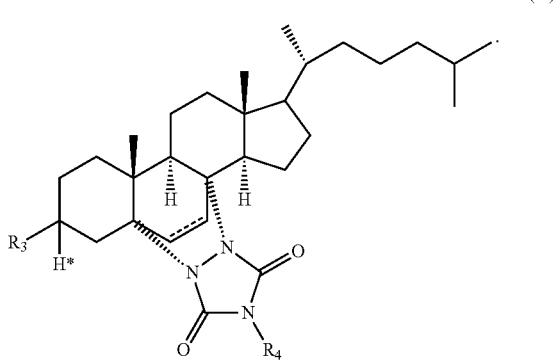

(Ic)

In certain embodiments, the compound of formula (I) is the compound of formula (Id), or a salt or solvate thereof:

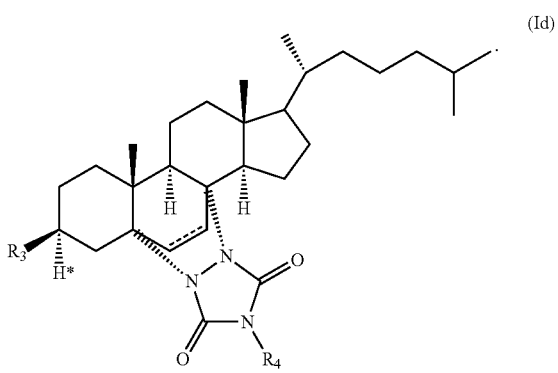

(Id)

In certain embodiments, $R_3$ is selected from the group consisting of —O(C$R_5$)$_n$$R_6$, —OC(=O)(C$R_5$)$_n$$R_6$, —OC(=O)(C$R_5$)$_n$O$R_5$, and —OC(=O)C($R_5$)=C($R_5$)$_2$.

In certain embodiments, the compound of formula (I) is selected from the group consisting of:

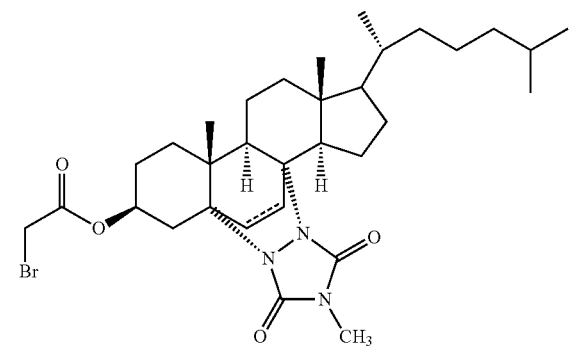

-continued

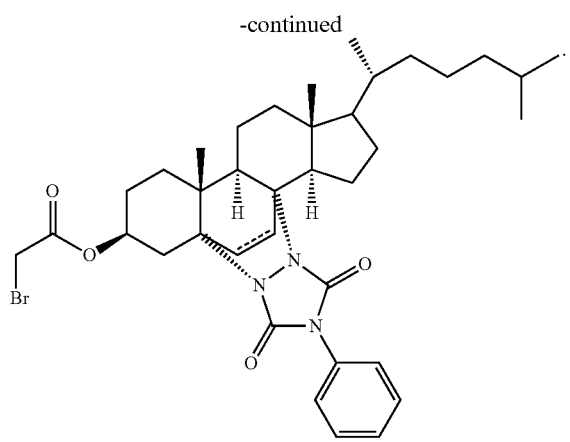

In certain embodiments, the cancer comprises at least one selected from the group consisting of breast cancer, prostate cancer, ovarian cancer, cervical cancer, skin cancer, pancreatic cancer, colorectal cancer, renal cancer, liver cancer, brain cancer, lymphoma, leukemia, lung cancer, endometrial cancer, neuroblastoma, and any combinations thereof. In other embodiments, the cancer comprises at least one selected from the group consisting of prostate cancer, breast cancer, ovarian cancer, endometrial cancer, medulloblastoma, neuroblastoma, melanoma, and any combinations thereof.

In certain embodiments, the subject is further administered at least one additional chemotherapeutic agent. In other embodiments, the chemotherapeutic agent is selected from the group consisting of alkylating agents; nitrosoureas; antimetabolites; antitumor antibiotics; plant alkyloids; taxanes; hormonal agents; anti-angiogenesis agents, and miscellaneous agents.

In certain embodiments, the subject is further administered at least one additional anti-angiogenesis agent. In other embodiments, the anti-angiogenesis agent is at least one selected from the group consisting of 2-methoxyestradiol AG3340, angiostatin, antithrombin-III, anti-VEGF antibody, VEGF antagonist, batimastat, bevacizumab, BMS-275291, CA1, canstatin, combretastatin, combretastatin-A4 phosphate, CC-5013, captopril, celecoxib, dalteparin, EMD121974, endostatin, erlotinib, gefitinib, genistein, halofuginone, ID1, ID3, IM862, omatinib mesylate, inducible protein-10, interferon-alpha, interleukin-12, lavendustin-a, LY317615, AE-941, merimastat, mapsin, medroxpregesteron acetate, Meth-1, Meth-2, Neovastat, osteopontin cleaved product, PEX, pigment epithelium growth factor, platelet growth factor 4, prolactin fragment, proliferin-related protein (PRP), PTK787/ZK222584, recombinant human platelet factor-4, restin, squalamine, SU5416, SU6668, suramin, taxol, tecogalan, thalidomide, thrombospondin, TNP-470, troponin I, vasostatin, VEGF1, VEGF-TRAP and ZD6474.

In certain embodiments, the compound of the invention and the additional agent are separately administered to the subject. In other embodiments, the compound of the invention and the additional agent are co-administered to the subject. In yet other embodiments, the compound of the invention and the additional agent are co-formulated.

In certain embodiments, the subject is a mammal. In other embodiments, the mammal is a human.

In certain embodiments, the composition is administered to the subject by at least one route selected from the group consisting of intravenous, oral, inhalational, rectal, vaginal, transdermal, intranasal, buccal, sublingual, parenteral, intrathecal, intragastrical, ophthalmic, pulmonary and topical routes.

In certain embodiments, the method further comprises procuring the compound of the invention for the subject.

Kits

The invention includes a kit comprising a compound of the invention, an applicator, and an instructional material for use thereof. The instructional material included in the kit comprises instructions for preventing or treating a disorder or disease contemplated within the invention in a subject. The instructional material recites the amount of, and frequency with which, the compound of the invention should be administered to the subject. In certain embodiments, the kit further comprises at least one additional chemotherapeutic agent. In other embodiments, the kit further comprises at least one additional anti-angiogenesis agent.

Combination Therapies

In certain embodiments, the compounds of the invention are useful in the methods of the invention in combination with at least one additional compound useful for treating or preventing cancer and/or uncontrolled angiogenesis. This additional compound may comprise compounds identified herein or compounds, e.g., commercially available compounds, known to treat, prevent or reduce the symptoms of cancer and/or uncontrolled angiogenesis.

In one aspect, the present invention contemplates that the compounds of the invention may be used in combination with a therapeutic agent such as an antitumor agent, including but not limited to a chemotherapeutic agent, an anti-cell proliferation agent or any combination thereof. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; anti-angiogenesis agents, and miscellaneous agents.

Alkylating agents are so named because of their ability to add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

Antitumor antibiotics generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include dactinomycin, daunorubicin, doxorubicin, idarubicin, mitomycin-C, and mitoxantrone.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells.

Examples of anti-angiogenesis agents include but are not limited to 2-methoxyestradiol (2-ME), AG3340, angiostatin, antithrombin-III, anti-VEGF antibody, batimastat, bevacizumab (Avastin), BMS-275291, CA1, canstatin, combretastatin, combretastatin-A4 phosphate, CC-5013, captopril, celecoxib, dalteparin, EMD121974, endostatin, erlotinib, gefitinib, genistein, halofuginone, ID1, ID3, IM862, omatinib mesylate, inducible protein-10, interferon-alpha, interleukin-12, lavendustin-a, LY317615, AE-941, merimastat, mapsin, medroxpregesteron acetate, Meth-1, Meth-2, Neovastat, osteopontin cleaved product, PEX, pigment epithelium growth factor (PEGF), platelet growth factor 4, prolactin fragment, proliferin-related protein (PRP), PTK787/ZK222584, recombinant human platelet factor-4 (rPF4), restin, squalamine, SU5416, SU6668, suramin, taxol, tecogalan, thalidomide, thrombospondin, TNP-470, troponin I, vasostatin, VEGF1, VEGF-TRAP and ZD6474. In some embodiments the anti-angiogenesis agent is a VEGF antagonist, such as a VEGF binding molecule (such as VEGF antibodies, or antigen binding fragment(s) thereof) or a VEGF antagonist such as NeXstar.

Miscellaneous agents include chemotherapeutics such as bleomycin, hydroxyurea, L-asparaginase, and procarbazine that are also useful in the invention.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas* exotoxin, *Clostridium difficile* Toxin B, *Helicobacter pylori* VacA, *Yersinia enterocolitica* YopT, Violacein, diethylenetriamine-pentaacetic acid, irofulven, Diptheria Toxin, mitogillin, ricin, botulinum toxin, cholera toxin, saporin 6, or a combination thereof.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, in particular a mammal, more particularly a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is advantageous to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In one embodiment, the compounds/compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. In particular, it is advantageously present in an amount from about 0.0005% to about 5% of the composition; more particularly, it is advantageously present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416;

WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies advantageously within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1: Synthesis

To a solution of commercially available 7 dehydrocholesterol (7DHC) (0.2 millimoles in ethyl acetate) and was added 1,2,4-triazolinedione (0.22 millimoles) under nitrogen atmosphere, and the system was stirred under the dark at 0-4° C. for 3 hours. The pink color eventually disappeared. The solvent was removed under vacuum.

The residue crude dry residue (0.07 millimoles) was added to a stirred suspension of bromoacetic acid and dicyclohexylcarbodiimide (DCC) in dichloromethane at 0-4° C. under a nitrogen gas atmosphere. The reaction mixture was stirred overnight, filtered to remove the resulting dicyclohexyl urea. The clear solution was evaporated and concentrated under reduced pressure to generate an oily residue, which was purified by preparative TLC.

The well resolved band was extracted with 20% methanol in dichloromethane, and the compound was isolated by evaporating the solvent under the reduced pressure, to produce a white to pale yellow solid (yield: 35-75% depending on the batch).

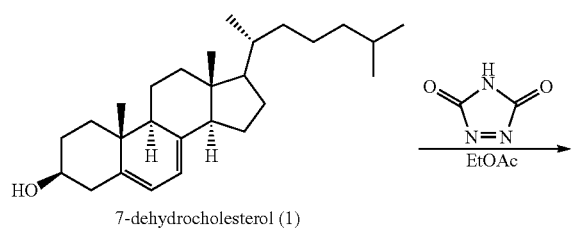

7-dehydrocholesterol (1)

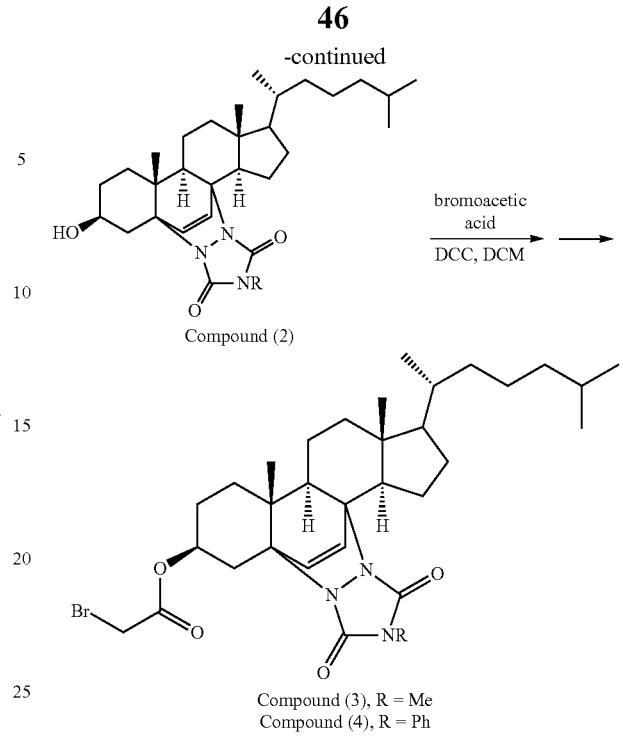

Compound (2)

Compound (3), R = Me
Compound (4), R = Ph

Example 2: Reduction of Cell Viability of Ovarian Cancer Cells

Exemplary compounds of the invention were tested in an ovarian cancer cell line (SKOV-3), using 7-dehydrocholesterol (7DHC) as a control.

SKOV-3 cells were seeded (5,000 cells/well) in complete DMEM (supplemented with 10% fetal bovine serum and 1% antibiotic) and allowed to adhere overnight. Media was replaced with a fresh complete DMEM media containing varying concentrations of the drugs of interest. DMSO was used as control. At a suitable interval (varying from 1 minute to 4 days), the media was replaced again with complete RPMI (supplemented with 10% fetal bovine serum and 1% antibiotic) containing MTS dye (Invitrogen Inc.) and incubated for a period varying from 10 minutes to 1 day. The absorbance of the media was read at varying wavelengths, advantageously at 492 nM in an ELISA reader.

FIG. 1 illustrates the reduction in cell viability of the SKOV-3 cells upon treatment with Compound (2).

Figure 2:
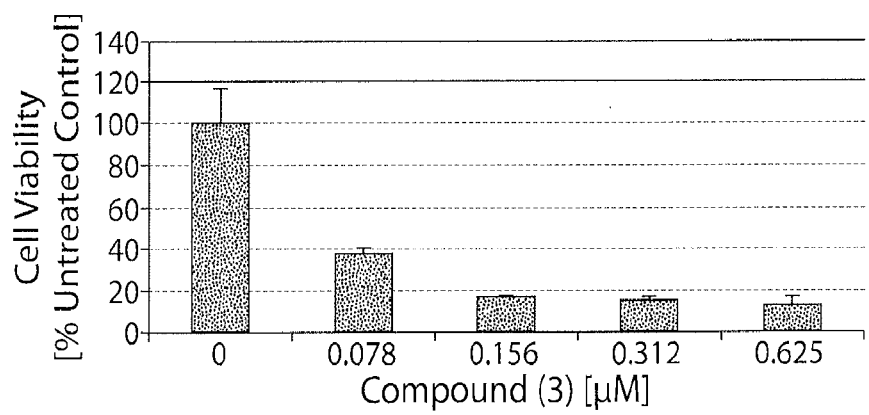
FIG. 2 is a bar graph illustrating the cytotoxic effect of a compound of the invention on SKOV-3 cells.

FIG. 2 illustrates the reduction in cell viability of the SKOV-3 cells upon treatment with Compound (3).

Example 3: Reduction of Cell Viability of Endometrial Cancer Cells

An exemplary compound of the invention (Compound (3)) was tested in an endometrial cancer cell line (ECC-1).

ECC-1 cells were seeded (10,000 cells/well) in complete RPMI (supplemented with 10% fetal bovine serum and 1% antibiotic) and allowed to adhere over night. Media was replaced with a fresh complete RPMI media containing varying concentrations of Compound (3). DMSO was used as control. At suitable intervals (varying from 1 minute to 4 days), the media was replaced again with complete RPMI (supplemented with 10% fetal bovine serum and 1% antibiotic) containing MTS dye (Invitrogen Inc) and incubated for period (varying from 10 min to 1 day). The absorbance of the media was read at varying wavelengths, advantageously at 492 nM in an ELISA reader.

Figure 3:
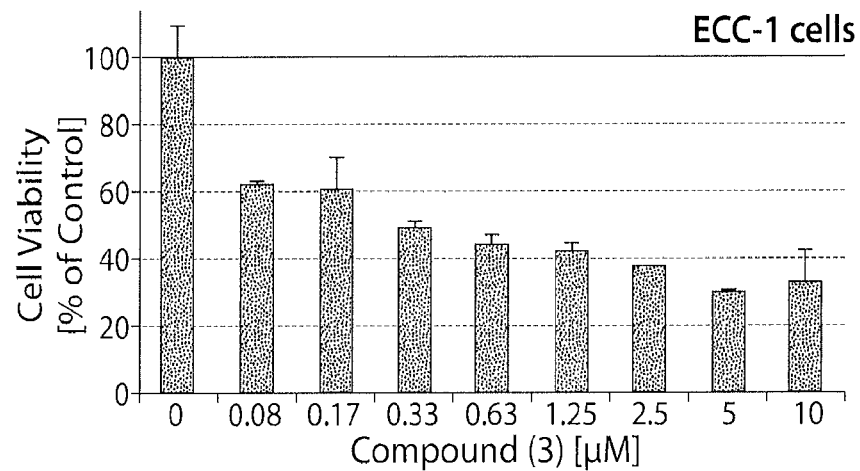
FIG. 3 is a bar graph illustrating the cytotoxic effect of a compound of the invention on ECC-1 cells.
Figure 4:
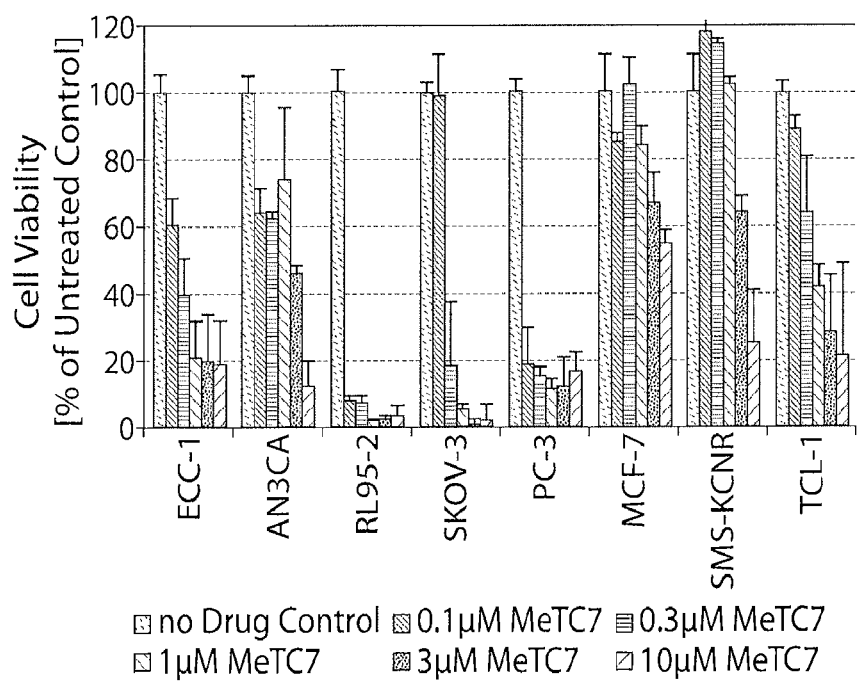
FIG. 4 is a bar graph illustrating the cytotoxic effect of a compound of the invention in a panel of ovarian and endometrial cancer, neuroblastoma, breast and prostate cancer cells. Also included are the relative cell viability of a third semester trophoblast treated with Compound (3).
Figure 5:
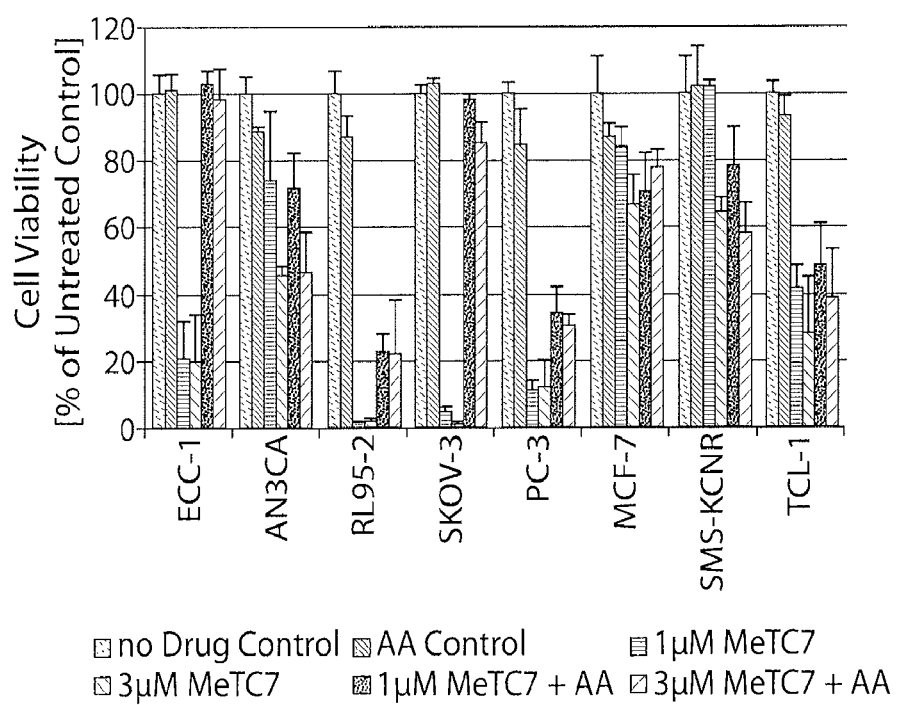
FIG. 5 is a bar graph illustrating the reduction in cytotoxic effects of a compound of the invention in a panel of ovarian cancer, endometrial cancer, prostate cancer, breast cancer and neuroblastoma upon pretreatment with ascorbic acid suggesting that compounds of the invention such as compound (3) lead to formation of lethal levels of reactive oxygen substrates (ROS) or radicals production.

FIG. 3 illustrates the reduction in cell viability of the ECC-1 cells upon treatment with Compound (3).

Example 4: Inhibition of Lipid Synthesis in Cancer Cells

Lipid synthesis in SKOV-3 cells treated with an exemplary compound of the invention was evaluated.

Figure 6A:
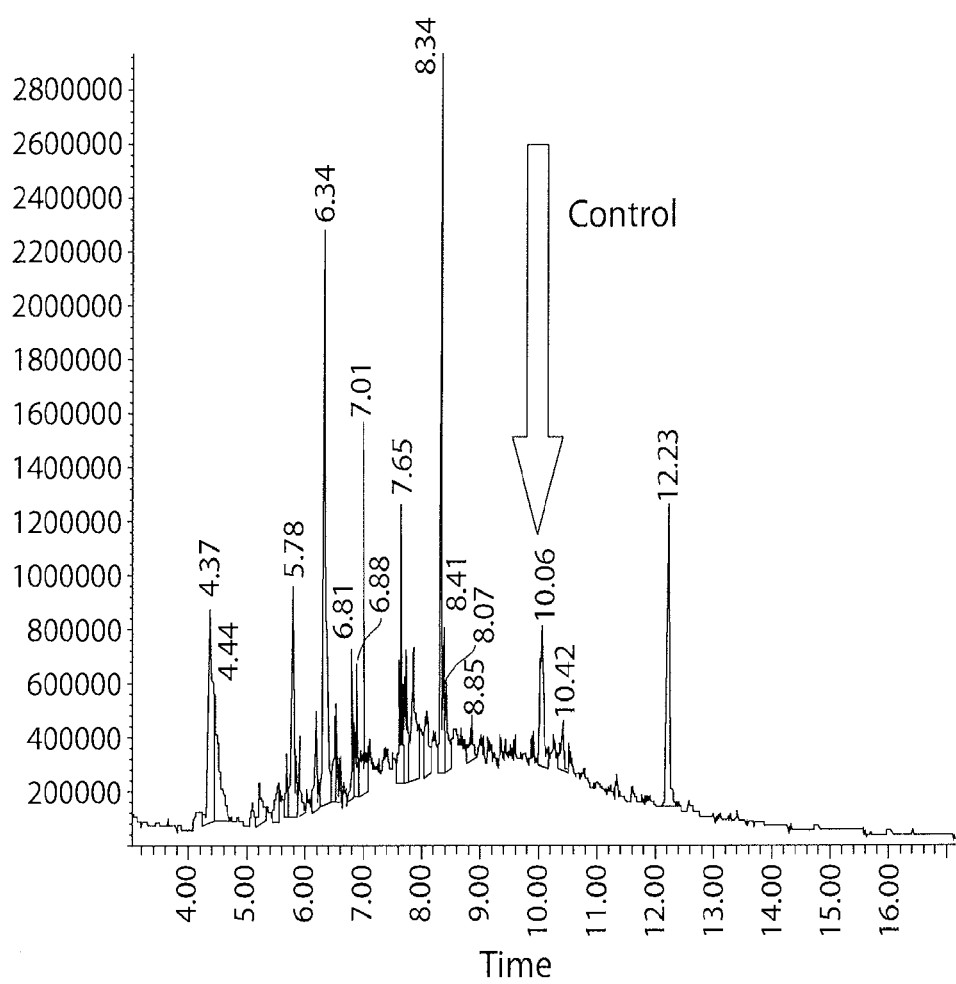
FIGS. 6A and 6B are a set of HPLC profiles of material extracted from untreated SKOV-3 cells (FIG. 6A) and SKOV-3 cells treated with Compound (3) (FIG. 6B).
Figure 6B:
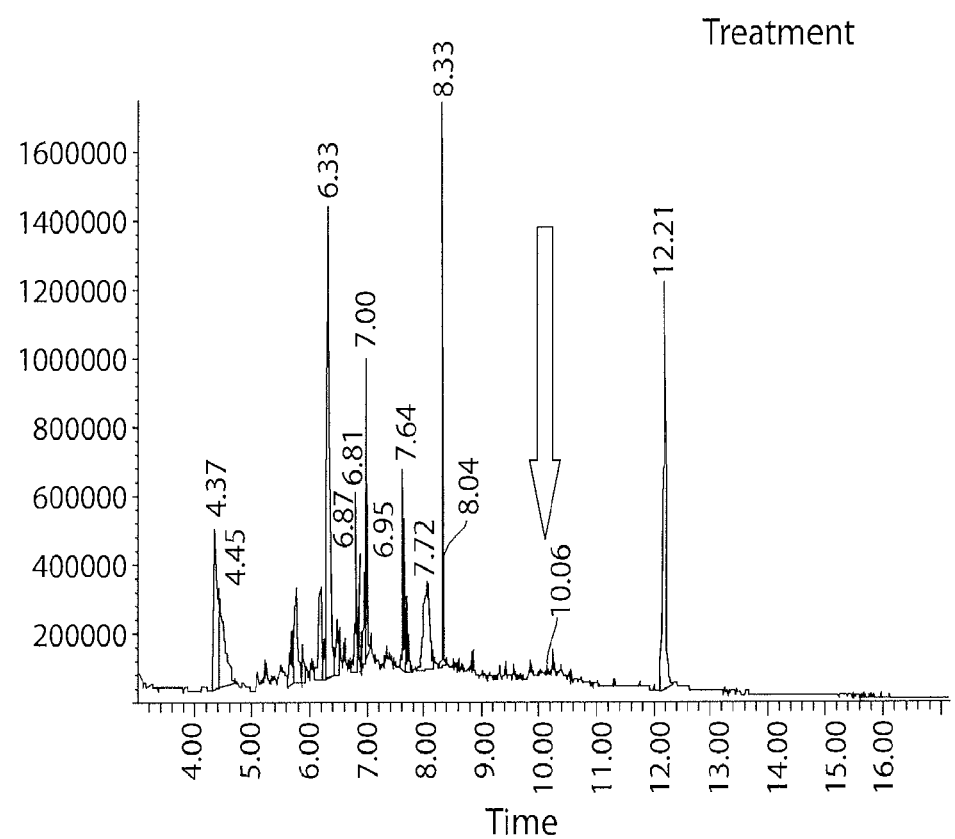

Approximately 3 million cells in serum free conditions were treated with Compound (3) (500 nM). Media was removed, and cells were washed with PBST, trypisinized and collected after centrifugation at 1,000 rpm. The cell pellet was washed with PBST and treated with methanolic HCl for 1 hour. The methanol was removed, and cells were suspended in water and extracted with chloroform. The collected chloroform layer was evaporated with a gentle nitrogen stream, and the residue was analyzed by HPLC. As illustrated in FIGS. 6A-6B, the lipids appearing at 10.06 minutes were significantly reduced upon the treatment with Compound (3), indicating that lipid synthesis had been inhibited by the compound of the invention.

Example 5: Xenographs

The effects of exemplary compounds of the invention on the growth of SKOV-3 tumor xenographs in nude mice were investigated. Substantively, four- to six week-old immuno-deficient nude mice (NU/NU; strain code 088/homozygous) (Charles River Laboratories, Wilmington, Mass.) were maintained at a temperature of 22±1° C. and a relative humidity of 55±5%, with a 12 h light/dark cycle. SKOV-3 cells were cultured to 80% confluence, washed in PBS twice, harvested by trypsination, pooled in complete medium, washed in PBS twice, and $2 \times 10^6$ cells/inoculate were suspended in 0.1 ml of matrigel and inoculated subcutaneously in the flank of mice. Mice with developing tumors after two weeks were randomly assigned to experimental groups. Compound (3) was prepared as a stock solution of 1 mM in 100% EtOH and diluted 1:40 in PBS for administration. Mice were treated intraperitoneally every other day with either vehicle control (control group; 7 animals) or 300 µl (10 mg/kg bwt) of MT19c (n=7) for 40 days. Mice were weighed and tumor size calculated using a caliper every 5 days.

Figure 7:
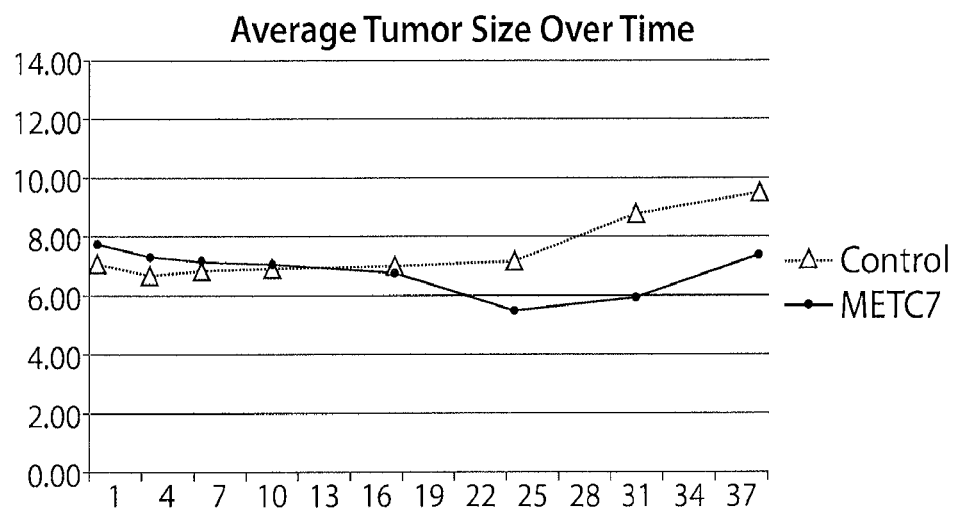
FIG. 7 is a graph illustrating the time-dependent overall tumor size in a xenograph model in nude mice.
Figure 8:
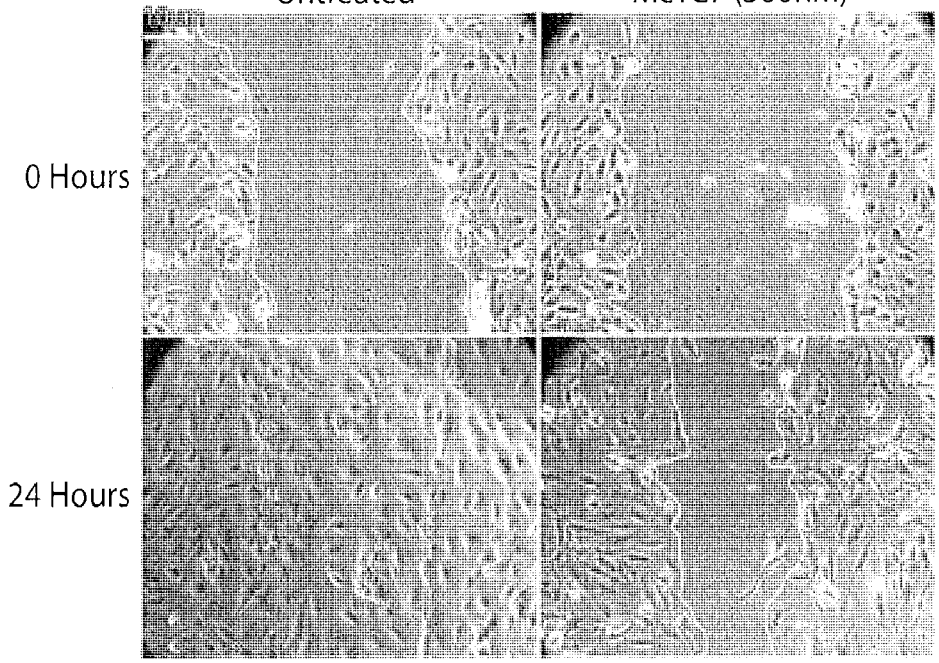
FIG. 8 illustrates the antiangiogenic effects of a compound of the invention via a wound healing assay model based on primary HUVEC cells.
Figure 9:
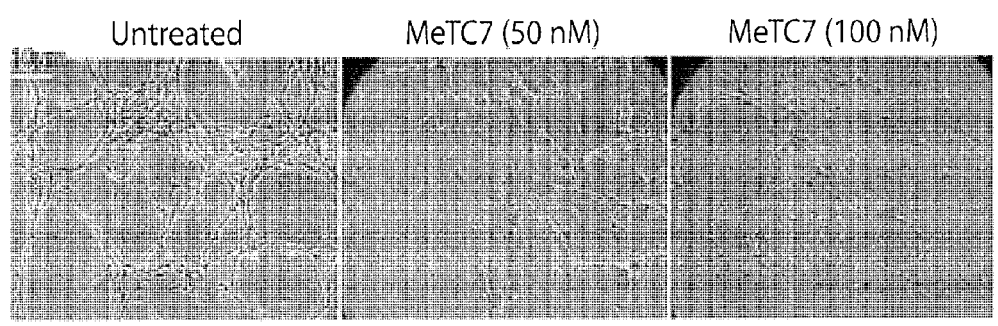
FIG. 9 illustrates the antiangiogenic effects of a compound of the invention via an ex vivo rat aorta ring assay. MeTC7 inhibited capillary formation and outgrowth in an ex vivo rat aorta assay (24 hour treatment).

FIG. 7 illustrates the finding that Compound (3) reduces the tumor burden in one such xenograph model.

Example 6: Reduction of Cell Viability of a Panel of Cancer Cell Lines

Cell lines derived from ovarian cancer, endometrial cancer, breast cancer, prostate cancer and neuroblastoma (5,000 cells/well) were seeded in complete DMEM (supplemented with 10% fetal bovine serum and 1% antibiotic) and allowed to adhere over night. Media was replaced with a fresh complete DMEM media containing varying concentrations of Compound (3). DMSO was used as control.

At suitable intervals (varying from 1 minute to 4 days), the media was replaced again with complete RPMI (supplemented with 10% fetal bovine serum and 1% antibiotic) containing MTS dye (Invitrogen Inc) and incubated for period (varying from 10 min to 1 day). The absorbance of the media was read at varying wavelengths, advantageously at 492 nm, in an ELISA reader Example 7: Ascorbic Acid Pretreatment in a Panel of Cancer Cell Lines Cell lines derived from ovarian cancer, endometrial cancer, breast cancer, prostate cancer and neuroblastoma (5,000 cells/well) were seeded in complete DMEM (supplemented with 10% fetal bovine serum and 1% antibiotic) and allowed to adhere over night. Cells were pretreated with 100 millimoles of acrorbic acid in 50 µL DMEM media for 3 hours. To the existing media was added DMEM media containing varying concentrations of 2× concentration of Compound (3). DMSO was used as control. At suitable intervals (varying from 1 minute to 4 days), the media was replaced again with complete RPMI (supplemented with 10% fetal bovine serum and 1% antibiotic) containing MTS dye (Invitrogen Inc) and incubated for period (varying from 10 min to 1 day). The absorbance of the media was read at varying wavelengths, advantageously at 492 nm, in an ELISA reader. As demonstrated, pretreatment with ascorbic acid reduced the cytotoxic effects of Compound (3) in a panel of cancer cell lines.

Example 8: Inhibition of Cell Migration in a Wound Healing Assay

A 24-well plate was coated with 100 µL of sterile 1% gelatin solution per well. After gelatin coating was hardened, about 100,000 HUVEC cells were seeded per well and allowed to grow to 100% confluence in EBM-2 media. A 200 µL pipette tip was then used to create a vertical scratch wound down the center of each well, and cells were washed once with fresh EBM-2 media. Cell monolayers were then imaged at a 0 h time point using light microscopy on an inverted microscope under sterile conditions. Wound areas were imaged again using light microscopy, and areas were demarcated on representative images.

Floating cells were removed and media was replaced with HUVEC cell media supplemented with vehicle or Compound (3) (500 nMoles) and incubated for 24 hours. The cells were imaged using a pre-cooled inverted NICON microscope (40×). The vehicle treated cells recovered the scratched area whereas compound (3)-treated cells failed to recover and repopulate the scratched area.

Example 9: Inhibition of Microcapillary Formation in a Rat Aorta Ring Assay

Rat aorta were harvested from the freshly euthanized naïve rats, cleaned and cut into fine rings and placed on matrigel beds prepared 30 min earlier in a 6 well plate. The aorta were allowed to stay there for 10 days, by which time microcapillaries were found to be sprouting. The media was replaced with fresh supplemented media and allowed the incubation for next 48 hours, thus affording a strong network of the microcappilary network. The media was replaced with fresh media containing vehicle or compound concentrations (50 nmoles and 100 nmoles) and incubated for 48 hours. The phase contrast images were recorded on a pre-cooled inverted NICON microscope.

Example 10: Antagonism of the Vitamin D Nuclear Receptor (VDR)

The assay was described in detail in Brard et al., 2011, Gynecologic Oncology. The biochemical interactions between MeTC7, its precursors such as 7-DHC or its adduct, and VDR were investigated using a fluorescence polarization assay. MeTC7 was incubated with VDR-LBD and a fluorescent labeled coactivator peptide (SRC2-3) in the presence and absence of calcitriol. In the presence of calcitriol, VDR interacts with the coactivator peptide SRC2-3. VDR antagonists disrupt this interaction by a direct or allosteric mode of inhibition.

Figure 10A:
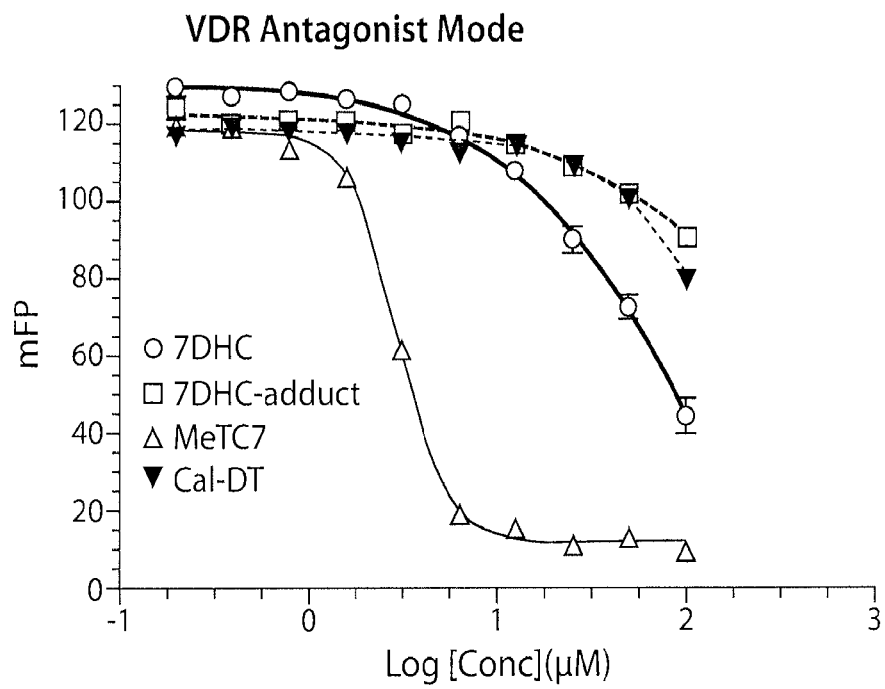
FIGS. 10A-10F illustrate the finding that compounds of the invention, as exemplified by Compound (3), are selective Vitamin D nuclear receptor (VDR) antagonists, as recited in Example 10.
Figure 10B:
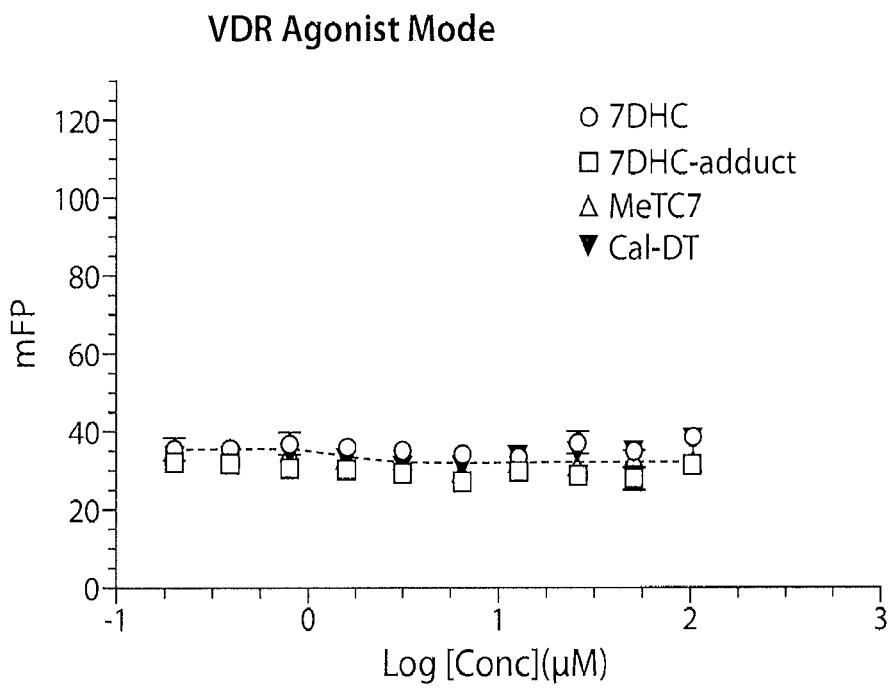
Figures 10C, 10D:
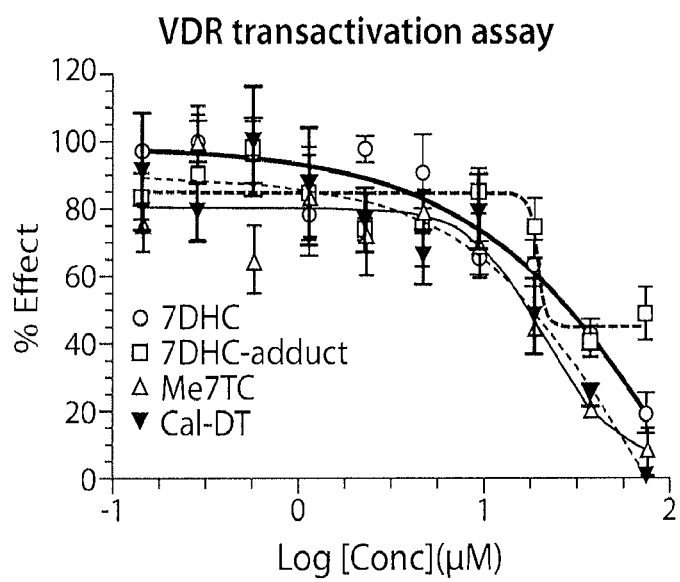

MeTC7 showed antagonistic effect at a concentration of 1.5-3 µM and higher (FIGS. 10A-10C). The ability of MeTC7 to bind to VDR and initiate the conformational change of VDR to allow coactivator recruitment was determined in the absence of calcitriol. Results show that MeTC7 is not a VDR agonist (FIG. 10B). FIG. 10D is a graph that illustrates results for the VDR transactivation assay (as % effect vs. log [Conc]).

Figure 10E:
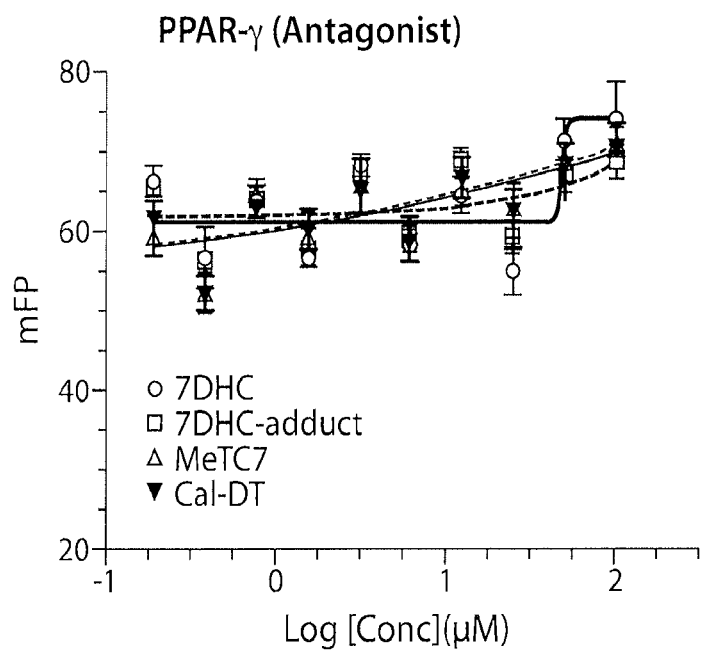
Figure 10F:
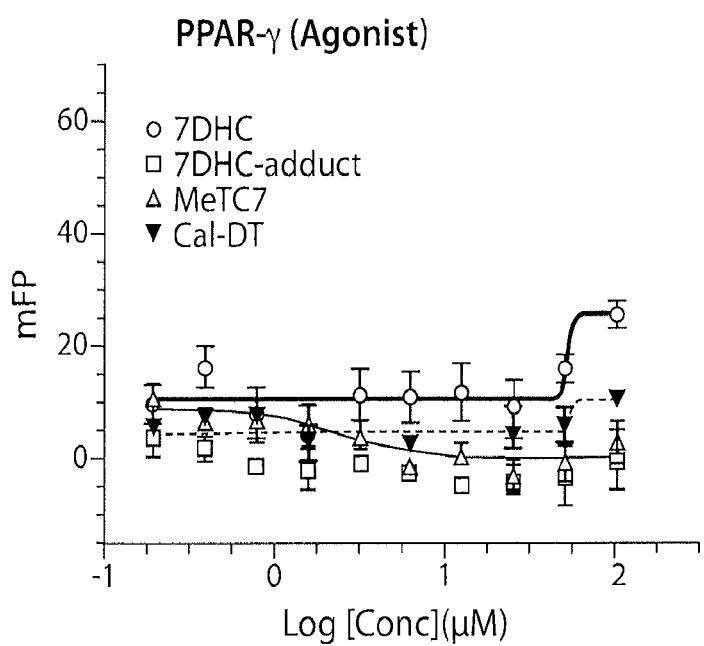

Determination of Agonistic/Antagonistic Properties of MeTC7 Using a PPARγ-Coactivator Binding Assay (FIGS. 10E-10F)

Briefly, pET15b-PPARγ-LBD expression plasmid, encoding the PPARγ-LBD (amino acids 173-475) was a generous gift from Gabor J. Tigyi (University of Tennessee, Memphis). PPARγ-LBD was expressed in BL21 (DE3) (Invitrogen), purified by affinity chromatography, and stored at −80° C. in buffer (50 mM Tris (pH 8.0), 25 mM KCl, 2 mM DTT, 10% glycerol, 0.01% NP-40). For the assay, MeTC7 or its precursors were serially diluted in DMSO and 100 nl of each concentration was transferred into 20 µL protein buffer (20 mM TRIS (pH 7.5), 100 mM NaCl, 0.01% NP-40, 2% DMSO, 10 nM DRIP2 (CNTKNHPMLMNLLKDNPAQD) labeled with Texas-Red maleimide, and 1 µM PPARγ-LBD) in the presence and absence of rosiglitazone (5 µM) in quadruplet using black 384 well plate (Costar, #3658). The samples were allowed to equilibrate for two hours. Binding was then measured using fluorescence polarization (excitation 595 nm, emission 615 nm) using a M1000 plate reader (Tecan). The experiments were evaluated using GraphPad Prism 5, and IC50 values were obtained by fitting the data to an equation (Sigmoidal dose-response-variable slope (four parameters). Values are given as the mean values of two independent experiments with a 95% confidence interval.

Example 11: Further Biological Characterization

FIGS. 11A-11C:

Viability of cell lines (ECC-1, AN3CA, RL-95-2, SKOV-3, PC-3, MCF-7, SMSKCNR and TCL-1) before and after MeTC7 treatment was determined by the CellTiter 96® AQueous One Solution Assay (Promega Corp, Madison, Wis.) following the manufacturer's recommendations. This colorimetric assay is based on the ability of mitochondria to reduce a substrate [MTS, 3-(4,5-dimethylthiazol-2-yl)-5-(3-carboxymethoxy phenyl)-2-(4-sulfophenyl)-2H-tetrazolium] into a soluble formazan product quantified by measuring the absorbance at 490 nm. The resulting OD is directly proportional to the number of living cells. Briefly, cells ($5 \times 10^3$/well) were plated into 96 well flat bottom plates (Corning, Inc., Corning, N.Y.) before treatment with various drugs or vehicle (DMSO) as indicated. Following incubation at 37° C. in a cell culture incubator for 20 h MTS reagent was added at a 1:10 dilution to the medium. The samples were incubated for an additional 4 h before absorbance was measured at 490 nm in an ELISA plate reader (Thermo Labsystems, Waltham, Mass.). Experiments were performed in triplicates; data are expressed as the mean of the triplicate determinations (X±SD) of a representative experiment in % of absorbance by samples with untreated cells [=100%]. Similarly, the cell viability of HEPG2 and HEK293 cells was determined except that the drug concentrations were used in the logarithmic values.

FIG. 11D:

SKOV-3 and OVCAR-8 ovarian cancer cells (10,000 per well) were seeded in a 8 well slide chamber in DMEM complete media and allowed to incubate overnight. Cells were treated with complete media containing either vehicle or MeTC7 (500 nM) and incubated for 12 hours in a humidified incubator maintained at standard conditions. DNA fragmentation was detected using the DeadEnd™ Fluorometric TUNEL System assay (Promega, Madison, Wis.) according to the manufacturer's recommendations. Fluorescence of apoptotic cells (green; labeling of DNA nicks by fluorescein-12-dUTP) and of chromatin (red; staining of chromatin with propidium iodide) was detected by fluorescence microscopy with an inverted microscope (Nikon Eclipse TE2000-E) and a 10× objective. Four randomly chosen microscopic fields were captured. For the detection of the cytochrome-C release as a marker of the apoptosis, the cells were fixed in 5% cold formalin solution and cells were stained with cytochrome-C primary antibody (Santa Cruz Biotechnology, USA) and corresponding fluorescence linked secondary antibody. The images were recorded using an inverted microscope. At least five field were arbitrarily scoped. A representative field is shown with abundant cytochrome-C release in the cytosol in the MeTC7 treated cells compared to the control which shows the concentrated staining of cytochrome-C in the nucleus.

FIG. 11E:

SKOV-3 and OVCAR-8 ovarian cancer cells were purchased from American Tissue Culture Collection (ATCC) (www dot atcc dot org) and maintained in DMEM media (Invitrogen Inc) supplemented with fetal bovine serum (10%) and antibiotics (1%). SKOV-3 cells (1 million each) were seeded in a 100 mm² petri dishes containing 5 mL of the complete DMEM media and cells were allowed to adhere and incubate overnight. Media was replaced with media containing vehicle or MeTC7 (500 nM) 12 hours. Media was collected and stored at −20° C. for future studies. Preparation of cell lysates, PAGE and immunoblotting with appropriate antibodies purchased from Origene (MD, USA) was carried out as previously described (Moore et al., Plos One, 2012, DOI: 10.1371/journal dot pone dot 0034443). Briefly, protein concentration of the remaining supernatant of the cell lysate was quantitated (BioRad protein estimation kit, Hercules, Calif.) and Western blotting was carried out. Samples were boiled in the presence of 5×SDS-PAGE sample buffer and 50 µg total cellular protein/lane were separated on 12% SDS-polyacrylamide gels and blotted onto PVDF membranes. The blots were blocked with 5% nonfat dry milk in PBST for 1 hr at room temperature and incubated overnight at 4° C. with the antibodies against caspase-7, 8 and cleaved PARP-1. After washing in PBST the blots were incubated with secondary antibody (peroxidase-conjugated antibodies; Amersham-Pharmacia Biotech, Piscataway, N.J.). The bands were visualized using horseradish peroxidase-conjugated secondary antibodies (Amersham-Pharmacia Biotech, Piscataway, N.J.) and documented by autoradiography (Fast Film, Phenix, Hayward, Calif.).

FIGS. 11F-11H:

Animal experiments were carried out in the animal facilities of Rhode Island Hospital (RIH), RI, USA with strict adherence to the guidelines of the Animal Welfare Committee of Rhode Island Hospital (RIH) and Women and Infants Hospital of Rhode Island (Laboratory Animal Protection Approval: A3922-01). Four to six week-old immunodeficient nude mice (NU/NU; strain code 088/homozygous)

Figure 11A:
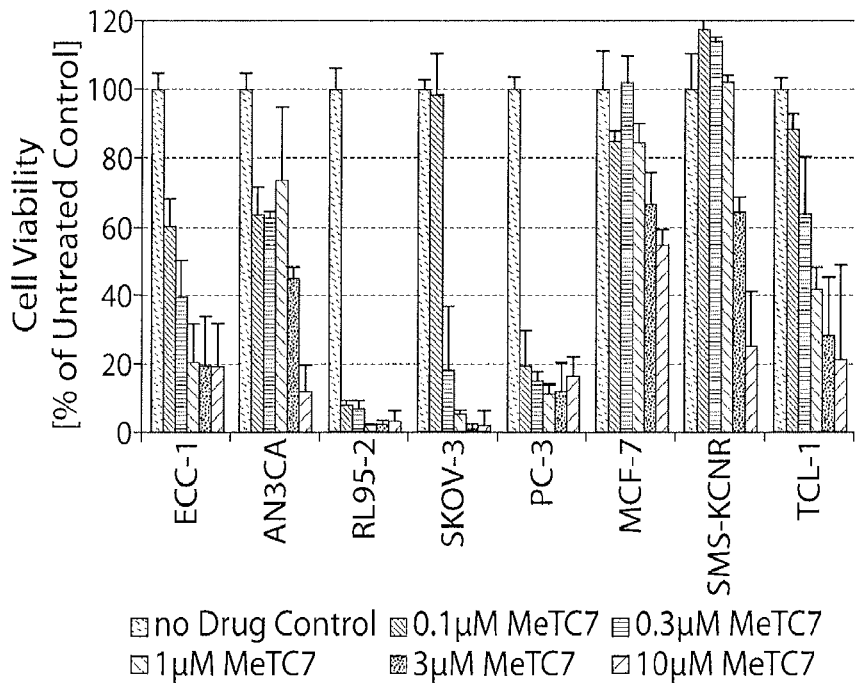
FIGS. 11A-11I illustrate the finding that compounds of the invention, as exemplified by Compound (3), block growth of various cancer cell lines, cause apoptosis and reduce the growth of ovarian cancer xenografts in animals, as recited in Example 11.
Figure 11B:
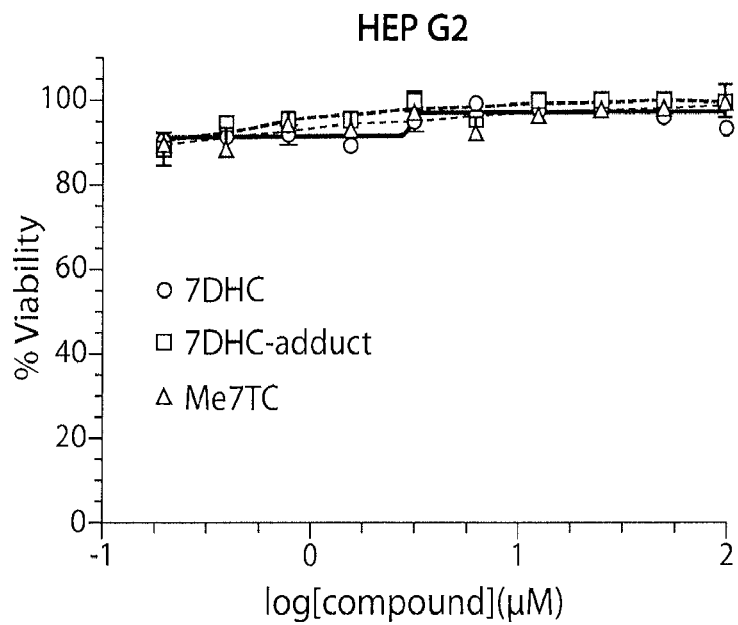
Figure 11C:
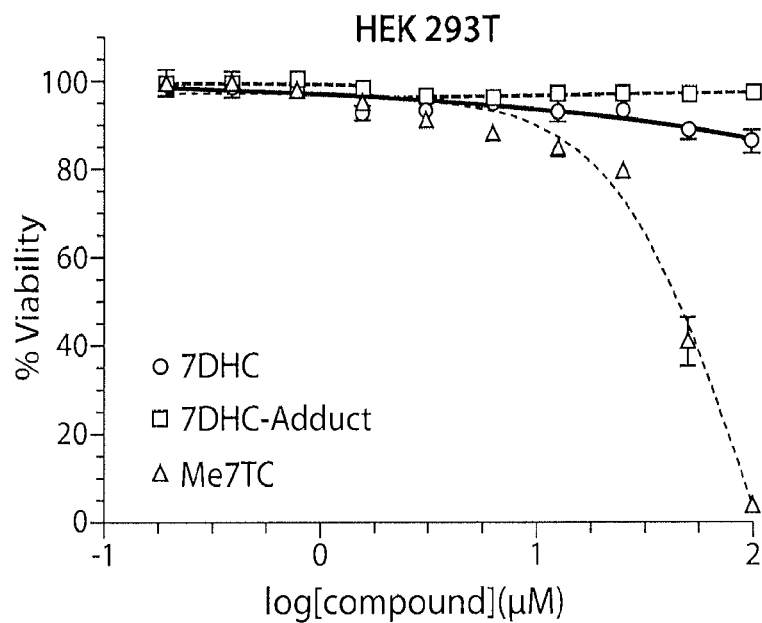
Figure 11D:
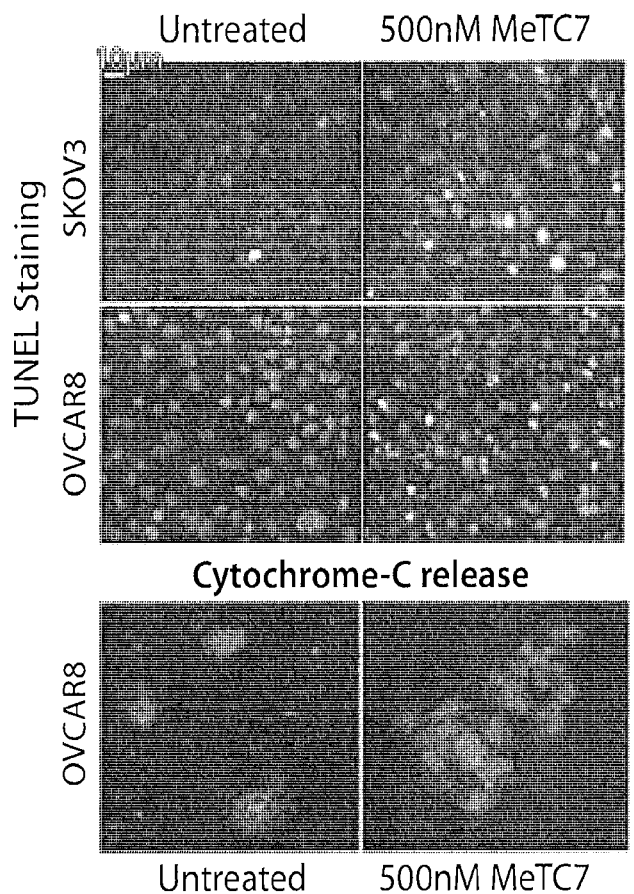
Figure 11E:
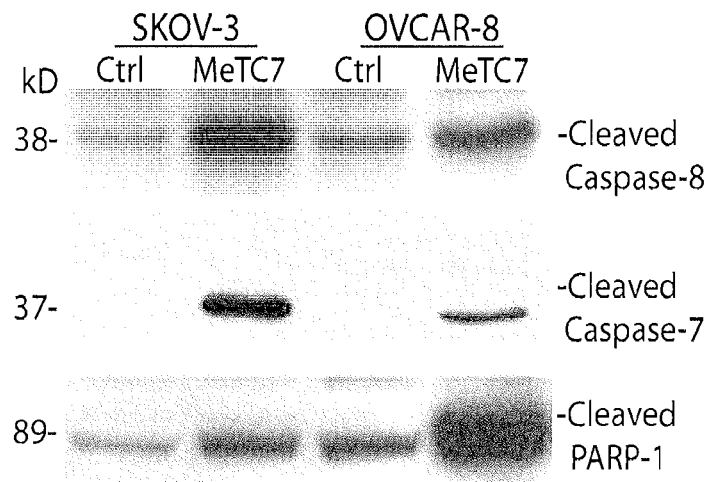
Figure 11F:
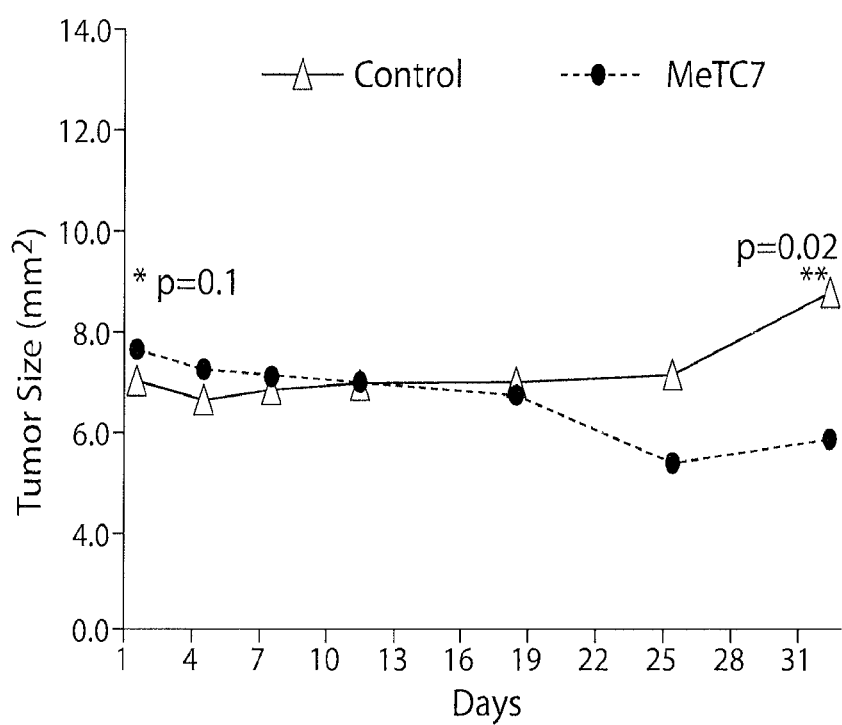
Figure 11G:
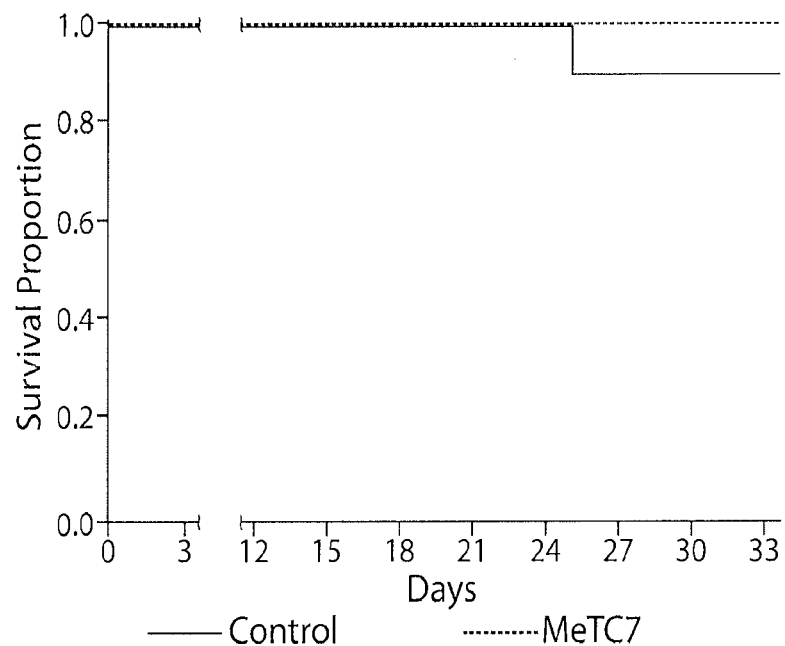
Figure 11H:
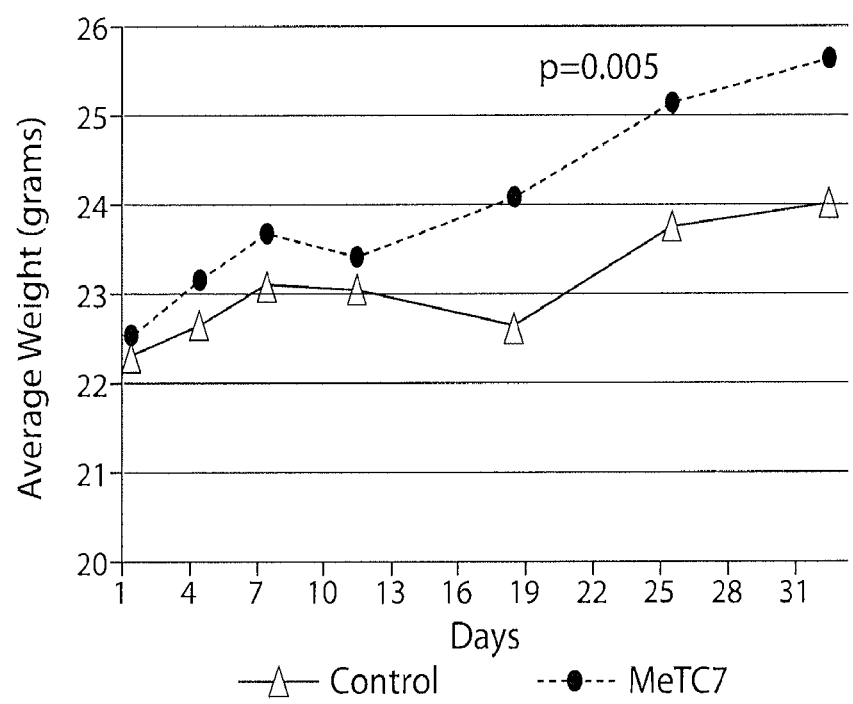

(Charles River Laboratories, Wilmington, Mass.) were maintained at a temperature of ~22° C. and a relative humidity of ~55%, with a 12 h light/dark cycle. SKOV-3 cells were cultured to 80% confluence, washed in PBS twice, harvested by trypsination, pooled in complete medium, washed in PBS twice, and 1×10⁶ cells/inoculate were suspended in 0.1 ml of matrigel and inoculated subcutaneously in the flank of mice. Mice with developing tumors after two weeks were randomly assigned to experimental groups. Mice were treated intraperitoneally every day with either vehicle control (control group; 6 animals) or MeTC7 (n=6, 10 mg/kg bwt, 5× week) for 31 days. Mice were weighed and tumor size were measured using a digital caliper on the days as indicated in the FIGS. 11F-11H. The survival curve of the animals survived during the course of the animal trial in treatment group compared to the control group (FIG. 11G) was estimated by the Kaplan-Meier analysis.

Figure 11I:
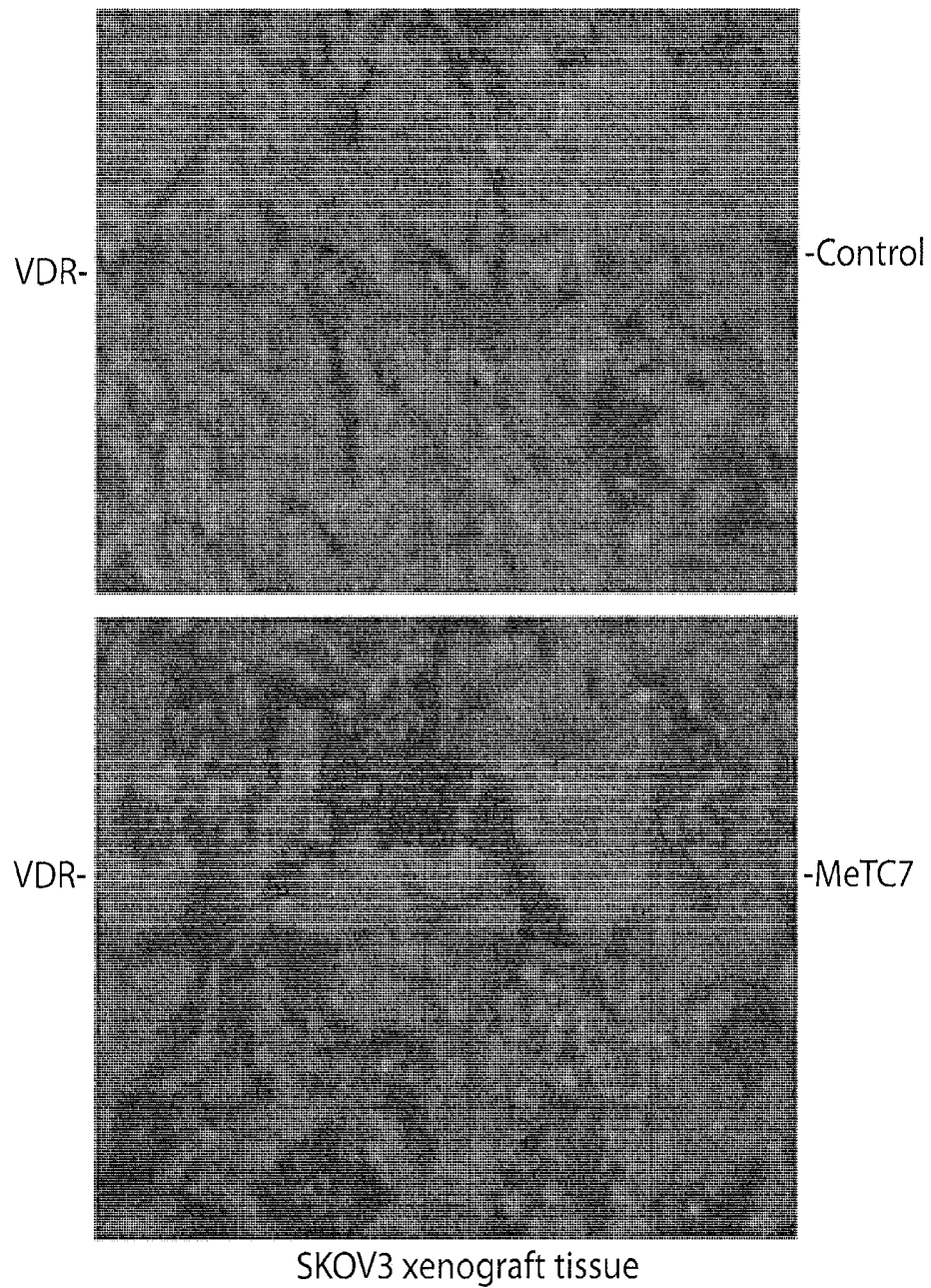
Figure 12:
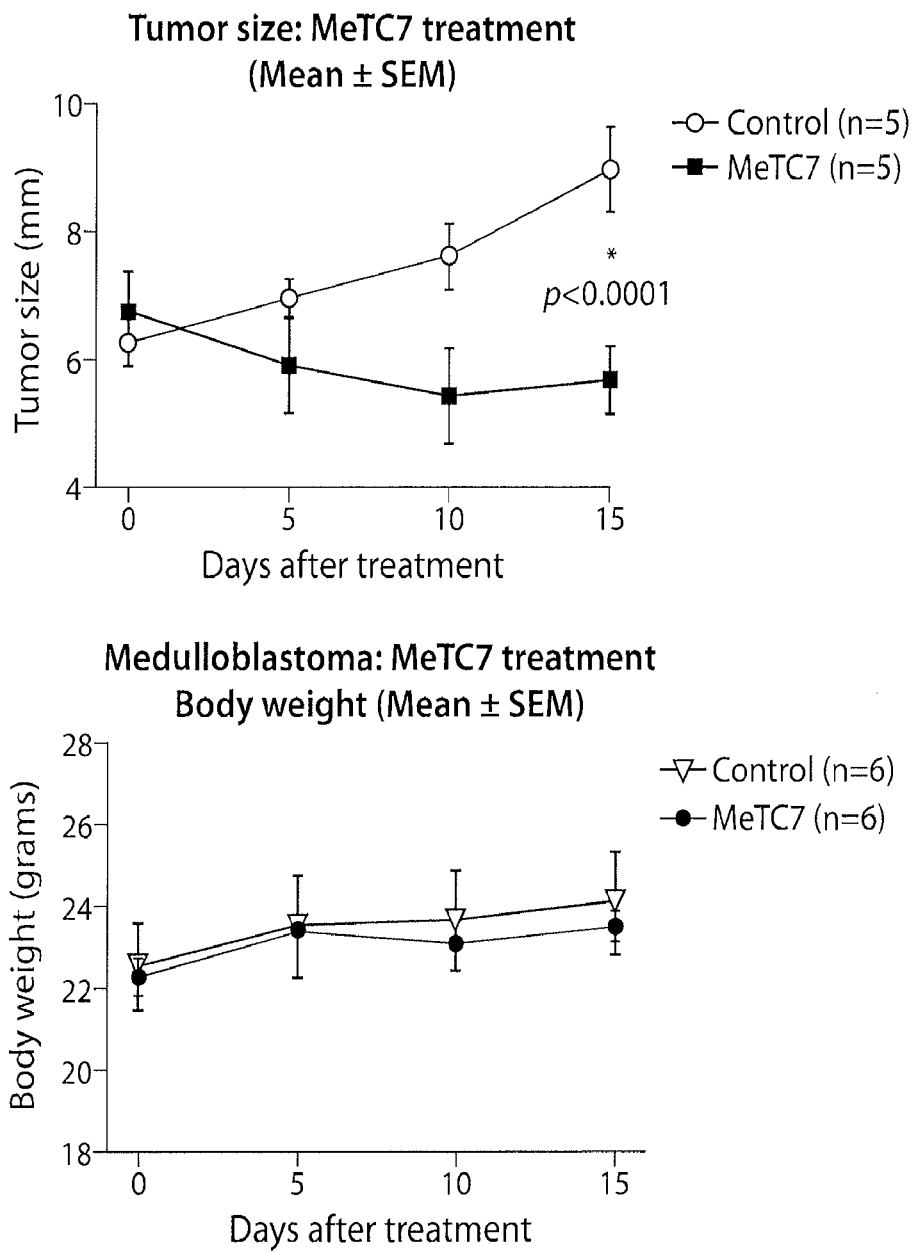
FIG. 12 is a set of graphs that illustrate the finding that compounds of the invention, as exemplified by Compound (3), reduce the growth of medulloblastoma xenografts in animals (Example 12). Exemplification includes time-dependent tumor size and body weight.
Figure 13:
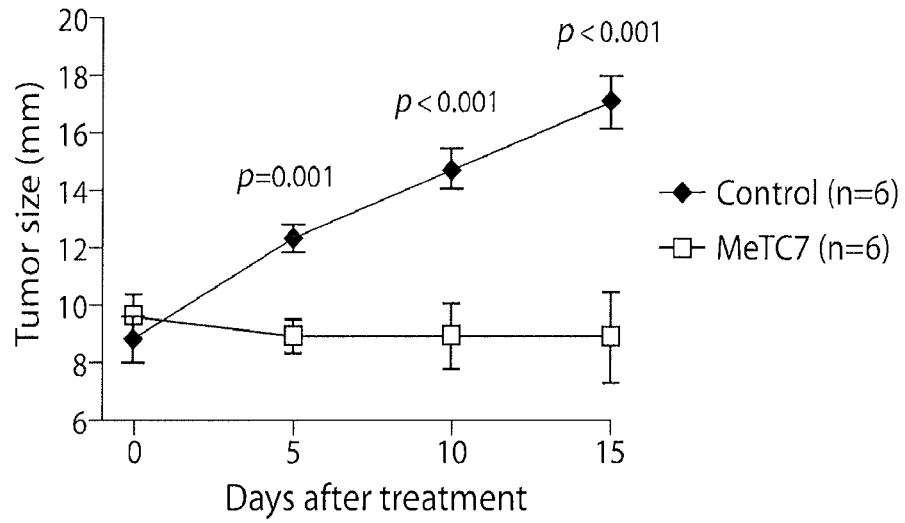
FIG. 13 is a set of graphs that illustrate the finding that compounds of the invention, as exemplified as Compound (3), reduce the growth of BRAF mutant melanoma xenografts in animals, extend survival in these animals (Example 13). Exemplification includes tumor size and survival analysis.
Figure 13:
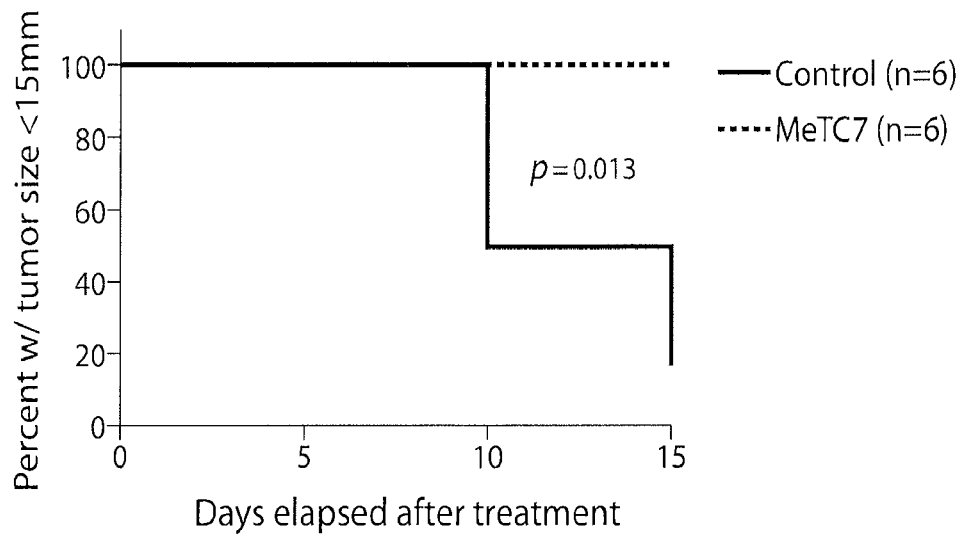

FIG. 11I:

The xenograft tissues from the animals of FIG. 11I were harvested after euthanasia and fixed in paraformaldehyde and embedded in paraffin. The slides of 5 μM were stained for the expression of VDR using the primary antibody (Santa Cruz Biotechnology, 1:50 dilution, USA) and corresponding fluorescence linked secondary and images were recorded as described previously (Moore et al., Plos One, 2012, DOI: 10.1371/journal dot pone dot 0034443).

Example 12: Medulloblastoma Xenograft

Animal experiments were carried out in the animal facilities of Rhode Island Hospital (RIH), RI, USA with strict adherence to the guidelines of the Animal Welfare Committee of Rhode Island Hospital (RIH) and Women and Infants Hospital of Rhode Island (Laboratory Animal Protection Approval: A3922-01). Four to six week-old immunodeficient nude mice (NU/NU; strain code 088/homozygous) (Charles River Laboratories, Wilmington, Mass.) were maintained at a temperature of ~22° C. and a relative humidity of ~55%, with a 12 h light/dark cycle. DAOY cells were cultured to 80% confluence, washed in PBS twice, harvested by trypsination, pooled in complete medium, washed in PBS twice, and 1×10⁶ cells/inoculate were suspended in 0.1 ml of matrigel and inoculated subcutaneously in the flank of mice. Mice with developing tumors after two weeks were randomly assigned to experimental groups. Mice were treated intraperitoneally every day with either vehicle control (control group; 6 animals) or MeTC7 (n=5, 10 mg/kg bwt, 5× week) for 15 days. Mice were weighed and tumor size were measured using a digital caliper every 5$^{th}$ days.

Example 13: Melanoma Xenograft

Animal experiments were carried out in the animal facilities of Rhode Island Hospital (RIH), RI, USA with strict adherence to the guidelines of the Animal Welfare Committee of Rhode Island Hospital (RIH) and Women and Infants Hospital of Rhode Island (Laboratory Animal Protection Approval: A3922-01). Four to six week-old immunodeficient nude mice (NU/NU; strain code 088/homozygous) (Charles River Laboratories, Wilmington, Mass.) were maintained at a temperature of ~22° C. and a relative humidity of ~55%, with a 12 h light/dark cycle. A2058 cells were cultured to 80% confluence, washed in PBS twice, harvested by trypsination, pooled in complete medium, washed in PBS twice, and 1×10⁶ cells/inoculate were suspended in 0.1 ml of matrigel and inoculated subcutaneously in the flank of mice. Mice with developing tumors after two weeks were randomly assigned to experimental groups. Mice were treated intraperitoneally every day with either vehicle control (control group; 7 animals) or MeTC7 (10 mg/kg bwt, 5× week) for 15 days. Mice were weighed and tumor size were measured using a digital caliper every 5$^{th}$ days. The percent of animals with tumor size less than 15 mm was calculated by Kaplan-Meier Analysis.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A compound of formula (I), or a salt or solvate thereof:

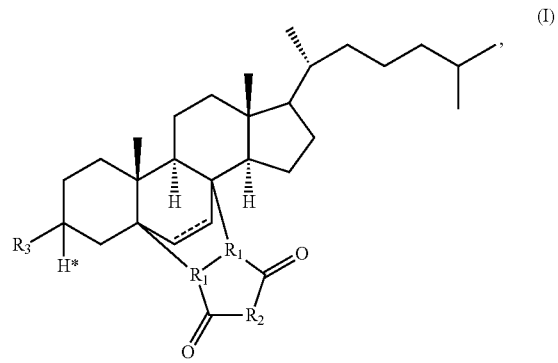

wherein in (I):
 $R_1$ is $CR_5$ or N, wherein:
  if $R_1$ is $CR_5$, then
   $R_3$ is selected from the group consisting of —O(CR$_5$)$_n$R$_6$, —O(CR$_5$)$_n$alkoxy, —O(CR$_5$)$_{n+1}$OH, —OC(=O)(CR$_5$)$_n$R$_6$ and —OC(=O)(CR$_5$)$_n$OR$_5$ and
  if $R_1$ is N, then $R_3$ is selected from the group consisting of —O(CR$_5$)$_n$R$_6$, —O(CR$_5$)$_{n+1}$OR$_5$, —OC(=O) (CR$_5$)$_n$R$_6$ and —OC(=O)(CR$_5$)$_n$OR$_5$;
 $R_2$ is selected from the group consisting of O, S, C(R$_4$)$_2$, and N(R$_4$);
 each occurrence of $R_4$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, substituted heteroarylalkyl, OR$_5$, and N(R$_5$)$_2$;
 each occurrence of $R_5$ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, and substituted heteroarylalkyl;
 $R_6$ is selected from the group consisting of F, Cl, Br, I, mesyl, tosyl, —OSi(R$_5$)$_3$, —C(=O)OR$_5$, and —C(=O)R$_5$;
 the dotted line is a single or double bond; and,
 n is an integer ranging from 1 to 5.

2. A compound of formula (I), or a salt or solvate thereof:

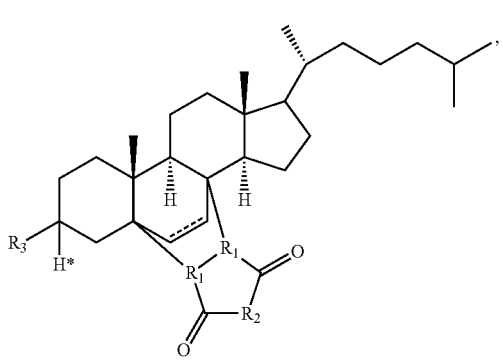

wherei in (I)

R₁ is N;

R₂ is N(R₄);

R₃ is selected from the group consisting of —O(CR₅)ₙR₆, —OC(=O)(CR₅)ₙOR₅, and —OC(=O)C(R₅)=C(R₅)₂;

R₄ is independently selected from the group consisting of H, alkyl, substituted alkyl, cycloalkyl, substituted cycloalkyl, alkenyl, substituted arylalkyl, heteroaryl, substituted heteroaryl, heteroarylalkyl, substituted heteroarylalkyl, OR₅, and N(R₅)₂;

each occurrence of R₅ is independently selected from the group consisting of H, alkyl, substituted alkyl, cycloalkyl, substituted cycloalkyl, alkenyl, substituted alkenyl, alkynyl, substituted alkenyl, aryl, substituted aryl, arylalkyl, substituted arylalkyl, heteroaryl, substituted heteroaryl, heteroarylalkyl, and substituted heteroarylalkyl;

R₆ is selected from the group consisting of F, Cl, Br, I, mesyl, tosyl, —OSi(R₅)₃, —C(=O)OR₅, and —C(=O)R₅;

the dotted line is a single or double bond; and, n is an integer from 1-10.

3. The compound of claim 2, wherein the compound of formula (I) is selected from the group consisting of:

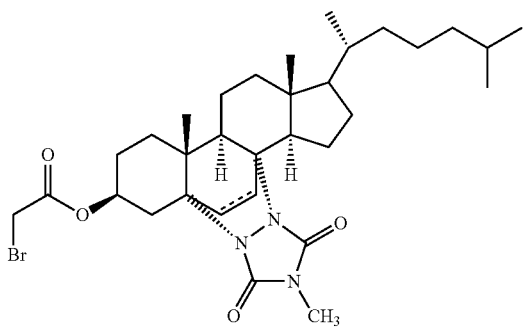

and

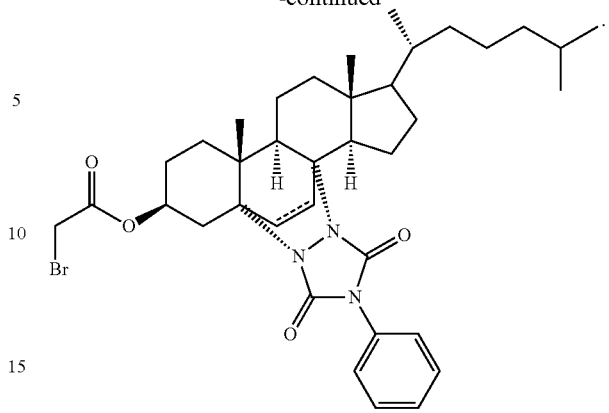

4. A compound of formula (I), or a salt or solvate thereof:

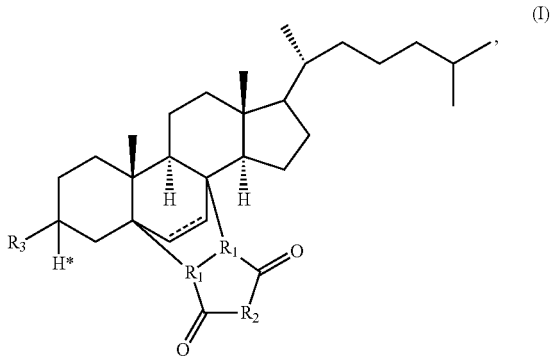

wherein in (I):

R₁ is CR₅;

R₂ is selected from the group consisting of O, S, C(R₄)₂, and N(R₄);

R₃ is selected from the group consisting of —N(R₅)₂, —NO, —N(R₅)N(R₅)₂, R₆, —N(R₅)—OR₅, —NH-C(=O)R₅, alkoxy, —OSO₃H, —O(CR₅)ₙalkoxy, —O(CR5)ₙ₊₁OH, —OC(=O)(CR₅)ₙR₆, —OC(=O)(CR₅)ₙOR₅, and —OC(=O)C(R₅)=C(R₅)₂ or R₃ is selected from the group consisting of =O and =S, and H* is omitted;

each occurrence of R₄ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, heteroaryl, substituted heteroaryl, heteroarylalkyl, substituted heteroarylalkyl, OR₅, and N(R₅)₂;

each occurrence of R₅ is independently selected from the group consisting of H, alkyl, substituted alkyl, cycloalkyl, substituted cycloalkyl, alkenyl, substituted alkenyl, alkynyl, substituted alkynyl, aryl, substituted aryl, arylalkyl, substituted alkenyl, heteroaryl, substituted heteroaryl, heteroarylalkyl, and substituted heteroarylalkyl;

R₆ is selected from the group consisting of F, Cl, Br, I, mesyl, tosyl, —OSi(R₅)₃, —C(=O)OR₅, and —C(=O)R₅;

the dotted line is a single or double bond; and, n is an integer from 1 to 10.

5. The compound of claim 4, wherein $R_5$ is selected from the group consisting of H, alkyl, substituted alkyl, cycloalkyl, substituted cycloalkyl, arylalkyl, substituted arylalkyl, heteroarylalkyl, and substituted heteroarylalkyl.

6. The compound of claim 4, wherein $R_3$ is selected from the group consisting of $R_6$, —O(CR$_5$)$_n$R$_6$, OC(=O)(CR$_5$)$_n$R$_7$, and OC(=O)C(R$_5$)=C(R$_5$)$_2$; or $R^3$ is selected from the group consisting of =O and =S, and H* is omitted.

7. The compound of any one of claims 1, 2 and 4, wherein the salt is an acid addition salt and is selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid, and any combinations thereof.

8. The compound of any one claims 1, 2 and 4 wherein the salt is a base addition salt and is selected from the group consisting of calcium, magnesium, potassium, sodium, ammonium, zinc, a basic amine salt, and any combinations thereof.

9. A pharmaceutical composition comprising the compound of any one of claims 1, 2 and 4 and a pharmaceutically acceptable carrier.

10. The composition of claim 9, further comprising at least one additional chemotherapeutic agent selected from the group consisting of alkylating agents; nitrosoureas; antimetabolites; antitumor antibiotics; plant alkyloids; taxanes; hormonal agents; anti-angiogenesis agents, and miscellaneous agents.

11. The composition of claim 9, further comprising at least one additional anti-angiogenesis agent selected from the group consisting of 2-methoxyestradiol AG3340, angiostatin, antithrombin-III, anti-VEGF antibody, VEGF antagonist, batimastat, bevacizumab, BMS-275291, CA1, canstatin, combretastatin, combretastatin-A4 phosphate, CC-5013, captopril, celecoxib, dalteparin, EMD121974, endostatin, erlotinib, gefitinib, genistein, halofuginone, ID1, ID3, IM862, omatinib mesylate, inducible protein-10, interferon-alpha, interleukin-12, lavendustin-a, LY317615, AE-941, merimastat, mapsin, medroxpregesteron acetate, Meth-1, Meth-2, Neovastat, osteopontin cleaved product, PEX, pigment epithelium growth factor, platelet growth factor 4, prolactin fragment, proliferin-related protein (PRP), PTK787/ZK222584, recombinant human platelet factor-4, restin, squalamine, SU5416, SU6668, suramin, taxol, tecogalan, thalidomide, thrombospondin, TNP-470, troponin I, vasostatin, VEGF1, VEGF-TRAP and ZD6474.

12. The composition of claim 10, wherein the compound and the agent are co-formulated in the composition.

13. A prepackaged pharmaceutical composition comprising at least one compound of any one of claims 1, 2 and 4.

14. The compound of claim 2, wherein the compound of formula (I) is

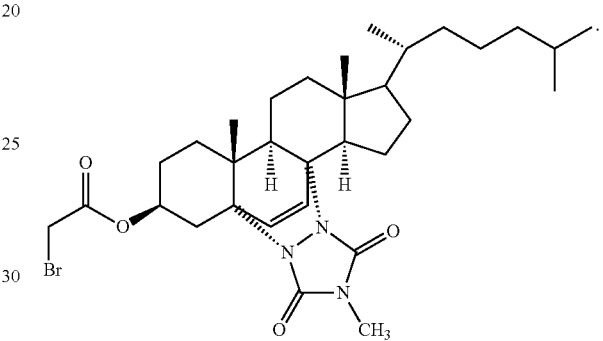

15. The compound of claim 8, wherein the basic amine is selected from the group consisting of triethylamine, diisopropylethylamine, trimethylamine, N,N'-dibenzylethylenediamine, chloroprocaine, choline, diethanolamine, ethylenediamine, meglumine, procaine and any combinations thereof.

* * * * *